(12) United States Patent
Miyanaga

(10) Patent No.: US 7,655,744 B2
(45) Date of Patent: Feb. 2, 2010

(54) BRANCHED POLYGLYCEROL-MODIFIED SILICONE

(75) Inventor: Seiichi Miyanaga, Wakayama (JP)

(73) Assignee: KAO Corporation, Tokyo (JP)

( * ) Notice: Subject to any disclaimer, the term of this patent is extended or adjusted under 35 U.S.C. 154(b) by 744 days.

(21) Appl. No.: 10/949,390

(22) Filed: Sep. 27, 2004

(65) Prior Publication Data

US 2005/0084467 A1 Apr. 21, 2005

Related U.S. Application Data

(63) Continuation of application No. PCT/JP03/03629, filed on Mar. 25, 2003.

(30) Foreign Application Priority Data

| Mar. 25, 2002 | (JP) | ............................. 2002-082845 |
| Mar. 14, 2003 | (JP) | ............................. 2003-069389 |
| Mar. 14, 2003 | (JP) | ............................. 2003-069390 |

(51) Int. Cl.
*C08G 77/04* (2006.01)
*C07F 7/08* (2006.01)

(52) U.S. Cl. ............................. 528/27; 528/29; 556/445

(58) Field of Classification Search ........................ None
See application file for complete search history.

(56) References Cited

U.S. PATENT DOCUMENTS

| 4,431,789 A | 2/1984 | Okazaki et al. |
| 5,145,915 A | 9/1992 | Weitmeyer et al. |
| 5,260,402 A | 11/1993 | Weitemeyer et al. |
| 5,306,838 A | 4/1994 | Shioya et al. |
| 6,150,311 A | 11/2000 | Decoster et al. |
| 6,417,323 B1 | 7/2002 | Miyanaga et al. |

FOREIGN PATENT DOCUMENTS

| JP | 57-149290 A | 9/1982 |
| JP | 2-265926 A | 10/1990 |
| JP | 4-20531 A | 1/1992 |
| JP | 5-98016 A | 4/1993 |
| JP | 6-234858 A | 8/1994 |
| JP | 7-238170 A | 9/1995 |
| JP | 9-71504 A | 3/1997 |
| JP | 9-278892 A | 10/1997 |
| JP | 9-302087 | * 11/1997 |
| JP | 10-316526 | 12/1998 |
| JP | 2000-38311 A | 2/2000 |
| WO | WO 99/42513 A1 | 8/1999 |

OTHER PUBLICATIONS

Andrianov, K. A. et al., Reactions of o-Allylphenol and of o-Allylphenoxy-Trimethylsilane with Alkoxy Alkyl Hydrogen Silanes, Mar. 27, 1962, Plastics Research Institute, USSR, 1948-1954.*

* cited by examiner

*Primary Examiner*—Sharmila Gollamudi Landau
*Assistant Examiner*—Trevor M Love
(74) *Attorney, Agent, or Firm*—Oblon, Spivak, McClelland, Maier & Neustadt, L.L.P.

(57) ABSTRACT

The invention provides a branched polyglycerol-modified silicone, silicon atoms of which are connected to at least one branched polyglycerol chain having one or more branched glycerol groups represented by the following formula (1) via a connecting group, a method for producing the same, and a cosmetic containing the same:

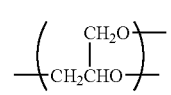

(1)

wherein, two oxygen atoms each independently bind to a glycerol or glycidol group represented by formula (1) above or the following formula (2), (3), or (4)

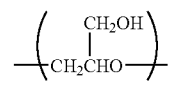

(2)

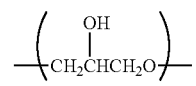

(3)

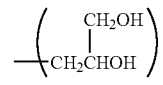

(4)

22 Claims, 20 Drawing Sheets

BRANCHED POLYGLYCEROL-MODIFIED SILICONE

CROSS REFERENCES TO RELATED APPLICATIONS

This application is a continuation of International Patent Application No. PCT/JP03/03629, filed on Mar. 25, 2003, and claims priority to Japanese Patent Application No. 2002-82845, filed on Mar. 25, 2002, Japanese Patent Application No. 2003-60389, filed on Mar. 14, 2003, and Japanese Patent Application No. 2003-69390, filed on Mar. 14, 2003.

FIELD OF THE INVENTION

The invention relates to a branched polyglycerol-modified silicone useful as an ingredient for cosmetics, fabric processing agent, and the like, a method for producing the same, and a cosmetic containing the same.

BACKGROUND OF THE INVENTION

Silicones are general-purpose materials having various advantages such as low intermolecular interaction, low reactivity, no toxicity or irritation, low friction coefficient, high lubricity, low viscosity, high plasticity, high insulation, and the like, and have been used in various industrial fields. However, silicones also carry the disadvantages that they are less compatible with aqueous solvents due to the high hydrophobicity thereof and extremely poorer in the wettability and the adsorptivity onto the surface of highly polar inorganic compounds, hair, skin, fabrics and other substrates. Another problems is that although the affinity to aqueous solvents may be improved to some degree by introducing polyethylene oxide chains, i.e., by the so-called polyether modification, it requires a large amount of the modifier as the polyethylene oxide group is inherently lower in hydrophilicity, thus leading to the relative decrease in the content of silicone and significantly impairing the advantages inherent in silicones. Highly polar functional groups such as an amino group and the like have been used as a modifier for improvement of the wettability and adsorptivity onto various media, but such groups also carried the problems of specific irritating odor, yellowing over time, and the like.

There were some reports on silicone compounds having a glycerol group. Japanese Patent Publication (JP-A) No. 57-149290 discloses a method of producing a silicone compound having polyglycerol groups via oxyalkylene groups as the connecting group, while JP-A No. 9-278892 discloses a silicone compound having polyglycerol groups via ester groups as the connecting group and a method of producing the same.

In addition, JP-A Nos. 10-316526 and 9-71504 disclose the applications thereof to cosmetics. All these applications utilize the silicones modified with polyglycerol groups that are aligned linearly in straight chains.

SUMMARY OF THE INVENTION

The invention provides a branched polyglycerol-modified silicone, having at least one branched polyglycerol chain containing at least one branched glycerol group represented by the following formula (1) and being connected via a connecting group, preferably via a connecting group containing an oxyphenylene group, to a silicon atom of the silicone; a method for producing the same, and a cosmetic containing the same.

[wherein, two oxygen atoms, independently of each other, bind to a glycerol or glycidol group represented by formula (1) above or the following formula (2), (3), or (4);

].

DETAILED DESCRIPTION OF THE INVENTION

Figure 1:
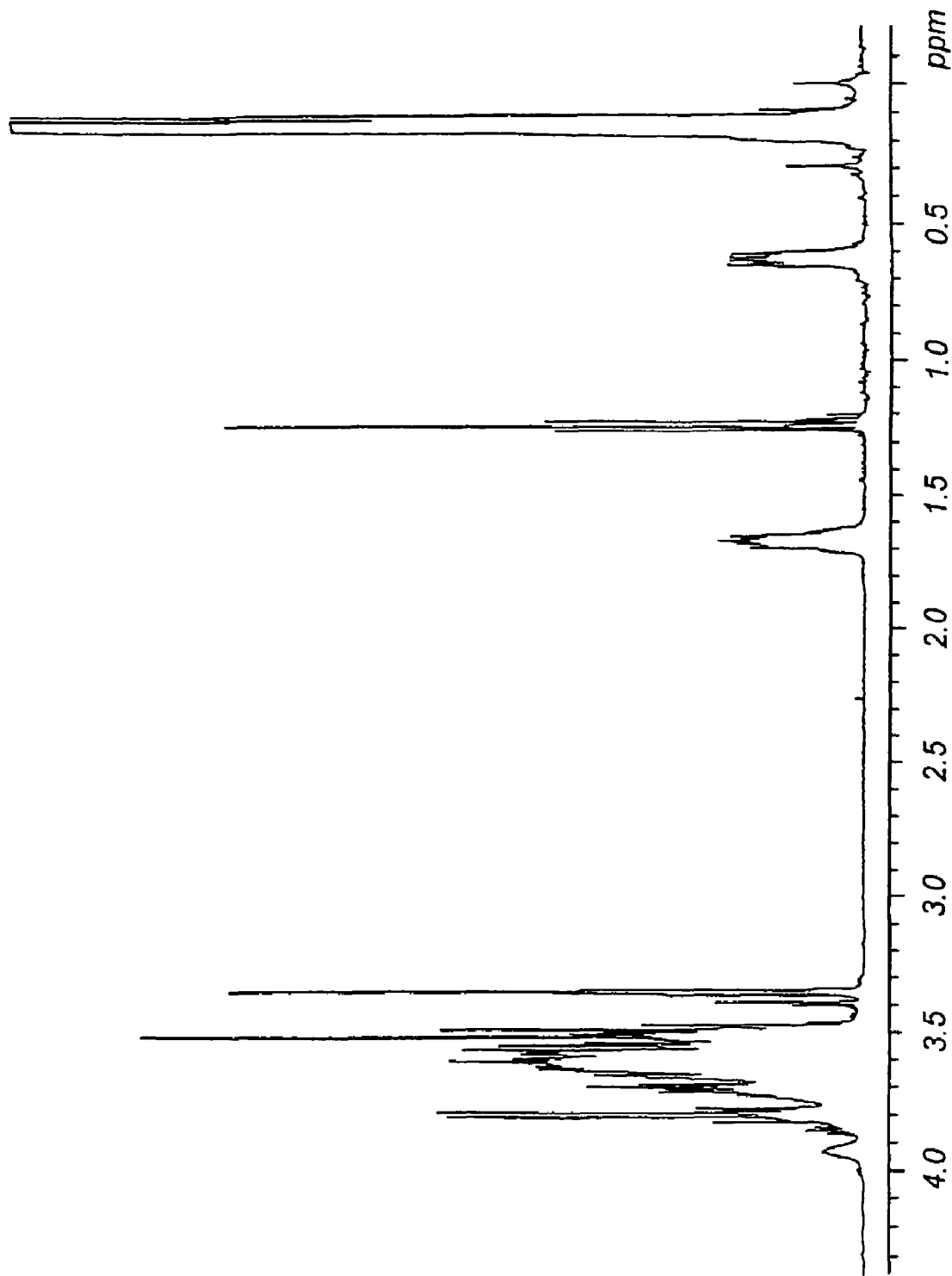
FIG. 1 is a $^1$H-NMR spectrum of the branched polyglycerol-modified silicone A obtained in Example 1.

The polyglycerol group linearly aligned in straight chains is rather hydrophilic than the polyoxyethylene group described above due to the presence of hydroxyl groups, but at the same time, has a molecular structure extremely unpreferable thermodynamically from the viewpoint of the adsorptivity onto media, as the skeletal polyalkylene chain is extremely flexible and movable. For that reason, silicones modified with linear polyglycerols were not satisfactory, for the purpose of connecting the silicones by adsorption, depositing by drying, coating, or film-forming onto various medium surfaces with the convenience of handling a liquid, which is made possible by dispersing or solubilizing the silicones in a hydrophilic solvent.

Further, all of the aforementioned methods of producing straight-chain polyglycerol-modified silicones employ a hydrosilylation reaction between a silicone hydride and a straight-chain polyglycerol derivative to which allyl groups are previously introduced, but the reaction had a drawback that it is inevitably accompanied with a side reaction between the hydrogen atoms of the extremely reactive silicone hydride and the many hydroxy groups present in the polyglycerol group, leading to non-reproducible increase in the viscosity of the reaction products and generation of a great amount of gel-like insoluble matters due to multifunctional reactions.

The preferred embodiments of the present invention relates to a novel hydrophilic silicone compound for use in extremely wider areas that is less irritating, less yellowing, superior in wettability and adsorptivity to various media while having high hydrophilicity and the advantages inherent in silicones all together.

In particular, the preferred embodiments of the present invention relates to a branched polyglycerol-modified silicone superior in chemical stability that is adsorbed firmly and efficiently on the surface of various media, skin, hair, fabrics and the like, even under the circumstances where they are treated in a hydrophilic solvent or washed thoroughly with running water after application and exhibits the various physical properties inherent in silicones and provides preferable touch feeling effectively.

Further, the present invention relates to a preferred method for producing the useful silicone compound reliably and reproducibly at low cost and in high yield without increase in viscosity or gelation.

Although not wanted to be limited to theory, the inventors have found that by generating a branched structure intentionally, i.e., by reacting two hydroxy groups of a glycerol group, which exhibits an extremely low adsorptivity alone or when it is aligned linearly in straight chain where the degree of dynamic molecular chain mobility is extremely high, with other glycerol groups and thus forming multiply branched polyglycerol chains, it was possible to confine many terminal hydroxy groups thereof in a narrow spatial region wherein free movement is restricted, thus enabling chelate-like multidentate adsorption and drastic improvement in adsorptivity of the molecule. The inventors also found that by connecting the multiply branched polyglycerol group with a high hydrophilicity to a hydrophobic unit such as silicone, it was possible to make the silicone more soluble in hydrophilic solvents and increase the adsorptivity thereof drastically at the same time with a smaller degree of modification.

The inventors have also found that it was possible to obtain a high-purity branched polyglycerol-modified silicone according to the invention without side reactions such as increase in viscosity, gelation, and the like, by adding a hydroxy group-containing epoxy compound, 2,3-epoxy-1-propanol, to a silicone having at least one functional group selected from the group consisting of hydroxy group, carboxy group, amino group, imino group, mercapto group and epoxy group, and by polymerizing it graftically in the presence of an acid or base catalyst.

The inventors have also found that it was possible to obtain a high-purity branched polyglycerol-modified silicone according to the invention reproducibly in an extremely high yield without side reactions such as increase in viscosity, gelation, and the like or significant decomposition of the silicone chains during the reaction, by adding a hydroxy group-containing epoxy compound, 2,3-epoxy-1-propanol, to a silicone having a phenyl group substituted with at least one hydroxy group or with at least one polyoxyalkylene group having a hydroxy group at its end, and by polymerizing it graftically in the presence of an acid or base catalyst.

[Branched Polyglycerol Chain]

In the invention, the branched polyglycerol chain has one or more branched glycerol groups represented by formula (1) [hereinafter, referred to as group (1)] as a branching unit. The structure of the branched polyglycerol chain includes "a" groups (1), "b" glycidol groups represented by formula (2) [hereinafter, referred to as group (2)], "c" glycerol groups represented by formula (3) [hereinafter, referred to as group (3)], and "d" glycerol groups represented by formula (4) [hereinafter, referred to as group (4)] as a terminal unit, which are bound to each other.

In the branched polyglycerol chain, groups (1), (2), and (3) may be bound to each other in any order. The oxygen atom in formula (2) binds to the glycerol group or glycidol group represented by formula (1), (2), (3) or (4); and the oxygen atom in formula (3) binds to a glycerol or glycidol group represented by formula (1), (2), (3) or (4). The branched polyglycerol chain has a more developed branched structure as the number of groups (1) increases and has a group (4) at the end of each branched chain.

The fact that the branched polyglycerol-modified silicone according to the invention contains one or more branching units of group (1) can be demonstrated easily by the presence of the peaks inherent in group (1) in a $^{13}$C-NMR spectrum as will be described below. Preferably, the mean number of group (1) units per a branched polyglycerol chain is 1 or more.

In the invention, the mean total number (a+b+c+d) of groups (1), (2), (3), and (4) per a branched polyglycerol chain is determined by the NMR analysis or comparison of the molecular weight with that of precursor silicone as described below, and preferably 3 or more, more preferably 3 to 201, even more preferably 3 to 101, even more preferably 3 to 51, and even more preferably 3 to 21 to provide the branched polyglycerol-modified silicone according to the invention with suitable silicone-like properties.

The degree of branching in the branched polyglycerol chain, a/(a+b+c+d), is preferably 1/20 to 1/2, even more preferably 1/10 to 1/2, and even more preferably 1/5 to 1/2, for providing the chain with a sufficiently high adsorptive activity.

Groups (1), (2), (3), and (4) may be bound to each other in any order in the branched polyglycerol chain.

The number of groups (1) (i.e., a) in each branched polyglycerol chain is preferably 1 to 100, more preferably 2 to 100, even more preferably 2 to 50, even more preferably 2 to 25, and even more preferably 2 to 10. The number of groups (4) (i.e., d) in each branched polyglycerol chain is preferably 2 to 101, more preferably 3 to 101, even more preferably 3 to 51, even more preferably 3 to 26, and even more preferably 3 to 11. The number of groups (2) (i.e., b) and groups (3) (i.e., c) may be the same or different from each other and are preferably 0 to 198, more preferably 0 to 196, even more preferably, 0 to 96, even more preferably, 0 to 46, and even more preferably 0 to 16.

[Connecting Group]

The connecting group connecting a silicon atom of the silicone in the branched polyglycerol-modified silicone according to the invention with the branched polyglycerol chain described above is a divalent group preferably having ether or ester groups.

The divalent group having ether groups is preferably a group represented by formula (5) [hereinafter, referred to as connecting group (5)]. The connecting group (5) binds to a silicon atom in the silicone chain at the $(R^1)_p$ side and to a branched polyglycerol chain at the $(AO)_q$ side.

(wherein, $R^1$ represents a straight- or branched-chain alkylene or alkenylene group having 1 to 22 carbons or an arylene group having 6 to 22 carbons which may have one or more substituents, preferably a straight- or branched-chain alkylene or alkenylene group having 1 to 22 carbons; AO represents an alkyleneoxy group having 1 to 4 carbons (also referred to as an oxyalkylene group) or an aryleneoxy group having 6 to 10 carbons (also referred to as an oxyarylene group), preferably an alkyleneoxy group having 1 to 4 carbons; p is a number of 0 or 1; q is a number of 0 to 30; and q AO's may be the same or different from each other.)

The divalent group having ester groups is preferably a group represented by formula (6) [hereinafter, referred to as connecting group (6)]. The connecting group (6) binds to a silicon atom in the silicone chain at the $R^2$ side and to a branched polyglycerol chain at the $(AO)_r$ side.

(wherein, $R^2$ represents a straight- or branched-chain alkylene or alkenylene group having 1 to 22 carbons or an arylene group having 6 to 22 carbons which may have one or more substituents, preferably a straight- or branched-chain alkylene or alkenylene group having 1 to 22 carbons; r is a number of 0 to 30; AO is the same as above; and r AO's may be the same or different from each other.)

Examples of the arylene groups in $R^1$ or $R^2$ in the connecting groups (5) and (6) includes alkylene arylene, arylene alkylene, and alkylene arylene alkylene groups. $R^1$ and $R^2$ each are preferably an alkylene or alkenylene group having 1 to 16 carbons, particularly preferably having 1 to 12 carbons, and examples thereof include methylene, ethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene and other groups. Among them, ethylene, propylene and trimethylene groups are more preferable, and an ethylene or trimethylene group is particularly preferable from the viewpoint of easiness in synthesis.

p may be 0 or 1, but is preferably 1 from the viewpoint of easiness in synthesis. q and r may be the same or different from each other, and are preferably 0 to 15, even more preferably 0 to 8, and even more preferably 0 to 5, even more preferably zero from the viewpoint of easiness in synthesis. q AO's and r AO's may be the same or different from each other, and bounded in any arrangement including alternating, random, block, and other regular sequences or in any other form. AO is preferably an ethyleneoxy, propyleneoxy, or phenyleneoxy group, and more preferably an ethyleneoxy group.

In the connecting groups (5) and (6), AO binds to a branched polyglycerol chain at the oxygen side of the alkyleneoxy or aryleneoxy group and to the ether or ester group contained in the connecting group at the alkylene or arylene side of the alkyleneoxy or aryleneoxy group.

Examples of the substituents in $R^1$ and $R^2$ include hydroxy, amino (having 1 to 22 carbons), imino (having 1 to 22 carbons), carboxy, alkoxy (having 1 to 22 carbons), and acyl (having 1 to 22 carbons) groups, and the like.

The connecting group is even more preferably a connecting group represented by the following formula (7) [hereinafter, referred to as connecting group (7)]. The connecting group (7) binds to a silicon atom in the silicone chain at the trimethylene side and to a branched polyglycerol chain at the oxygen atom side.

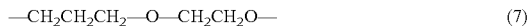

The connecting group in the branched polyglycerol-modified silicone according to the invention connecting a silicon atom in the silicone chain and the branched polyglycerol chain described above preferably contains oxyphenylene groups. Among the connecting groups above, a group represented by the following formula (8) [hereinafter, referred to as connecting group (8)] or a group represented by formula (9) [hereinafter, referred to as connecting group (9)] is preferable. The connecting group (8) binds to a silicon atom in the silicone chain at the $(R^3)_u$ side and to a branched polyglycerol chain at the $(AO)_v$ side. The connecting group (9) binds to a silicon atom in the silicone chain at the $(R^4)_z$ side and to branched polyglycerol chains at the $(AO)_x$ and $(AO)_y$ sides.

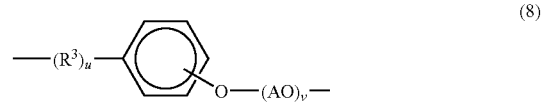

(wherein, $R^3$ represents a straight- or branched-chain alkylene or alkenylene group having 1 to 22 carbons which may have one or more substituents; u is a number of 0 or 1; v is a number of 0 to 30; AO is the same as above; and v AO's may be the same or different from each other.)

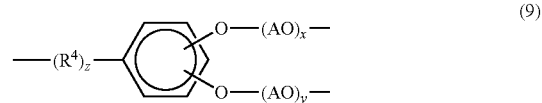

(wherein, $R^4$ represents a straight- or branched-chain alkylene or alkenylene group having 1 to 22 carbons which may have one or more substituents; z is a number of 0 or 1; x is a number of 0 to 30; y is a number of 0 to 30; AO is the same as above; and x and y AO's may be the same or different from each other.)

In the connecting groups (8) and (9), $(R^3)_u$ and $(R^4)_z$ each are a group connecting a silicon atom in the silicone chain to the phenylene group of the oxyphenylene group contained in the connecting group of the invention; $R^3$ and $R^4$ each are preferably an alkylene or alkenylene group having 1 to 16 carbons, particularly preferably having 1 to 12 carbons; and examples thereof include ethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, and other groups. Among them, an ethylene, propylene or trimethylene group is more preferable, and an ethylene or trimethylene group is even more preferable from the viewpoint of easiness in synthesis.

Substituents which may be present on $R^3$ and $R^4$ include hydroxy, amino (having 1 to 22 carbons), imino (having 1 to 22 carbons), carboxy, alkoxy (having 1 to 22 carbons), and acyl (having 1 to 22 carbons) groups and the like.

u and z may be 0 or 1, but are preferably 1 from the viewpoint of easiness in synthesis.

In the connecting groups (8) and (9), AO is an oxyalkylene or oxyarylene group connecting a branched polyglycerol chain to the oxygen atom of the oxyphenylene group contained in the connecting group of the invention, which binds to the branched polyglycerol chain at the oxygen side of the oxyalkylene or oxyarylene group and to the oxygen atom of the oxyphenylene group at the alkylene or arylene side of the oxyalkylene or oxyarylene group. AO is preferably an oxyethylene, oxypropylene or oxyphenylene group, and among them, an oxyethylene group is particularly preferable.

v, x and y each are a number of 0 to 30, preferably 0 to 15, more preferably 0 to 5, even more preferably zero from the viewpoint of easiness in synthesis and reaction. If v, x and y are not 0, v AO's, x AO's, and y AO's may be the same or different from each other, and bound in any arrangement including alternating, block, and other regular sequences, or in a random manner.

In the connecting group (8), the position of two substituents, the oxygen atom and the $(R^3)_u$ group (a silicon atom in the silicone chain, if u is 0), on the phenylene unit of the oxyphenylene group may be ortho, meta, or para, or a mixture thereof. In the connecting group (9), the position of either two of three substituents, two oxygen atoms and the $(R^4)_z$ group (a silicon atom in the silicone chain, if z is 0), on the phenylene unit of the oxyphenylene group may be ortho, meta, or para, or a mixture thereof, respectively.

Among the oxyphenylene group-containing connecting groups according to the invention, even more preferable is a connecting group represented by the following formula (10) [hereinafter, referred to as connecting group (10)]. The connecting group (10) binds to a silicon atom in the silicone chain at the trimethylene side and to a branched polyglycerol chain at the oxygen atom side.

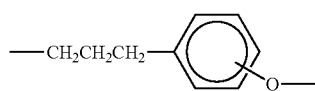

(10)

In the connecting group (10), the position of two substituents, the oxygen atom and the trimethylene group, on the phenylene unit in the oxyphenylene group may be be ortho, meta, or para, or a mixture thereof, and ortho, para, or a mixture thereof is preferable from the viewpoint of easiness in synthesis.

[Branched Polyglycerol-Modified Silicone]

The silicone constituting the branched polyglycerol-modified silicone according to the invention is a derivative of a polysiloxane having two or more silicon atoms, and the polysiloxane may have any structure such as straight-chain, branched-chain, or cyclic. The number-average molecular weight of the polysiloxane is preferably 300 to 700,000, more preferably 300 to 200,000, and even more preferably 1,000 to 20,000. The number-average molecular weight can be determined by gel permeation chromatography (hereinafter, referred to as GPC), light scattering, or the like, as will be described below.

The branched polyglycerol-modified silicone according to the invention is preferably a straight-chain silicone represented by formula (11) [hereinafter, referred to as silicone (11)].

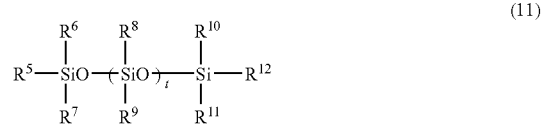

(11)

(wherein, $R^5$, $R^6$, $R^7$, t $R^8$'s, t $R^9$'s, $R^{10}$, $R^{11}$, and $R^{12}$ may be the same or different from each other, and each represents a connecting group bound to a branched polyglycerol chain; a straight- or branched-chain alkyl, alkenyl, or alkoxy group having 1 to 22 carbons; or an aryl group having 6 to 22 carbons which may be substituted with fluorine atoms; at least one of $R^5$, $R^6$, $R^7$, t $R^8$'s, t $R^9$'s, $R^{10}$, $R^{11}$, and $R^{12}$ is a connecting group bound to the branched polyglycerol chain; and t is a number of zero to 10,000.)

In the silicone (11), $R^5$, $R^6$, $R^7$, t $R^8$'s, t $R^9$'s, $R^{10}$, $R^{11}$, and $R^{12}$ excluding the connecting group bound to a branched polyglycerol chain may be the same or different from each other and each are a straight- or branched-chain alkyl, alkenyl, or alkoxy group having 1 to 22 carbons, or an aryl group having 6 to 22 carbons which may have a substituent or be substituted with a fluorine atom. Examples of the alkyl groups having 1 to 22 carbons include methyl, ethyl, propyl, isopropyl, butyl, t-butyl, pentyl, hexyl, heptyl, octyl, nonyl, trifluoropropyl, and the like; examples of the alkenyl groups having 1 to 22 carbons, vinyl and allyl groups; and examples of the alkoxy groups having 1 to 22 carbons, methoxy, ethoxy, propoxy, butoxy, pentyloxy, hexyloxy, heptyloxy, octyloxy, phenoxy groups and the like. Among them, a straight- or branched-chain alkyl group having 1 to 12 carbons, vinyl group, allyl group, or aryl group having 6 to 12 carbons is preferable; an alkyl group having 1 to 3 carbons or phenyl group is more preferable; and a methyl, propyl, or phenyl group is even more preferable. Among them, a methyl group is even more preferable from the viewpoint of versatility and price, while a phenyl group is more preferable from the viewpoint of heat resistance.

In the silicone (11), the substituents which the groups $R^5$ to $R^{12}$ may have are, for example, phenyl, phenol, hydroxy, carboxy, amino (having 0 to 14 carbons), imino, (aminoethyl) amino, (dimethylaminoethyl)amino, polyoxyalkylene, mercapto, epoxy groups, and the like. A propyl group is particulary preferable as the base structure of $R^5$ to $R^{10}$ when they have above substituents.

In the silicone (11), at least one, preferably 1 to 10, even more preferably 1 to 5, and particularly preferably 1 to 2 of the groups $R^5$, $R^6$, $R^7$, t $R^8$'s, t $R^9$'s, $R^{10}$, $R^{11}$, and $R^{12}$ are the connecting groups bound to a branched polyglycerol chain.

These connecting groups may be located at the side chain and/or one end or both ends of the silicone (11), or at the mixed sites thereof.

When one group selected from the group consisting of $R^5$ to $R^7$ and one group selected from the group consisting of $R^{10}$ to $R^{12}$, are the connecting groups bound to a branched polyglycerol chain and the remaining groups of $R^5$ to $R^7$ and $R^{10}$ to $R^{12}$, t $R^8$'s, and t $R^9$'s are the other groups, the branched polyglycerol-modified silicone according to the invention very preferably becomes a branched polyglycerol-modified silicone substituted at both ends, which easily forms a higher-order structure binding to each other in water or other solvents. In such a case, the other groups of $R^5$ to $R^7$ and $R^{10}$ to $R^{12}$, t $R^8$'s, and t $R^9$'s each are preferably a methyl group.

When three or more connecting groups bound to a branched polyglycerol chain are present in t $R^8$'s and t $R^9$'s, the branched polyglycerol-modified silicone according to the invention preferably becomes a branched polyglycerol-modified silicone multi-substituted at the side chains, which is superior in hydrophilicity and adsorptive ability.

t in the silicone (11) is a number of 0 to 10,000, preferably 1 to 3,000, even more preferably 5 to 500, and even more preferably 10 to 150.

The number-average molecular weight of the branched polyglycerol-modified silicone according to the invention is preferably 500 to 500,000, more preferably 750 to 200,000, and even more preferably 1,000 to 100,000. The number-average molecular weight is determined by GPC (with the reference of standard polystyrene or polyethylene glycol), as will be described below.

The ratio of the total number (G) of groups (1), (2), (3), and (4) in the branched polyglycerol chains (hereinafter, referred to as the total number of glycerol groups) to the number of silicon atoms (Si) in the branched polyglycerol-modified silicone according to the invention, (G/Si), is preferably 0.001 to 50, more preferably 0.05 to 10, even more preferably 0.1 to 3, and even more preferably, 0.15 to 1. In this range, the modified silicone exhibits a high residual adsorptivity rate on various materials, skin, hair, and fabrics.

In the branched polyglycerol-modified silicone according to the invention, the branched polyglycerol chain may have a small amount of ethyleneoxy and/or propyleneoxy groups in the range that does not significantly impair the advantageous features of the branched polyglycerol-modified silicone according to the invention, i.e., the silicone-like characteristics, the hydrophilic property, and high-adsorpitivity described above. The ethyleneoxy and/or propyleneoxy groups may be present randomly in the branched polyglycerol chain, or multiple ethyleneoxy and/or propyleneoxy groups may be present blockwise in consecutive chains in the branched polyglycerol chains. In that case, the blocks of multiple ethyleneoxy and/or propyleneoxy groups may be present either in the neighborhood of the connecting group of the branched polyglycerol chain or at the end or middle thereof. If the ethyleneoxy and/or propyleneoxy groups are present, the ethyleneoxy and/or propyleneoxy groups are present in an amount of preferably 0.001 to 0.5 molar equivalence and more preferably 0.02 to 0.2 molar equivalence with respect to 1 molar equivalence of the glycerol group.

[Method of Synthesizing Branched Polyglycerol-Modified Silicones]

From the common knowledge of the industrial process technique for modified silicones, the branched polyglycerol-modified silicone according to the invention may seem to be properly produced by using hydrosilylation reaction between a silicone hydride and an allylpolyglycerolether as raw materials but it is more preferable to use the following production method, as the silicone hydrides often cause the problems of an increase in viscosity, gelation, and the like by facile condensation with hydroxy groups in the polyglycerol chains.

That is, it is possible to obtain the branched polyglycerol-modified silicone according to the invention without any problem, by adding 2,3-epoxy-1-propanol (hereinafter, referred to as glycidol) to a silicone having one or more functional groups selected from the group consisting of hydroxy, carboxy, amino, imino, mercapto and epoxy groups (hereinafter, referred to as precursor silicone) in the presence of an acid or base catalyst and allowing graft polymerization of the mixture.

Preferable examples of the precursor silicones include hydroxy silicones having one or more groups represented by the following formula (12) connected to the silicon atom of the silicone; carboxy (or the salt thereof) silicones having one or more groups represented by the following formula (13) connected thereto; amino or imino silicones having one or more groups and a group represented by the following formula (14) connected thereto; mercapto silicones having one or more groups represented by the following formula (15) connected thereto; and epoxy silicones having one or more groups and a group represented by the following formula (16) or (17) connected thereto. These functional groups may be bound either to the side chain, one end, or both ends of the silicone chain. The functional group is preferably a hydroxy or epoxy group, from the viewpoint of easiness in starting a reaction.

(wherein, $R^1$, p, q, and AO are the same as above.)

(wherein, $R^2$, r, and AO are the same as above.)

(wherein, $R^{13}$ is a straight- or branched-chain alkylene or alkenylene group having 1 to 22 carbons or an arylene group having 6 to 22 carbons; X and Y are the same or different from each other and each are a hydrogen atom, a hydrocarbon group having 1 to 22 carbons which may have a hydroxyl group, or an aminoalkyl group having 1 to 22 carbons which may have a hydroxy group; and at least one of X and Y is a hydrogen atom or an aminoalkyl group having a hydrogen atom on the amino group.)

(wherein, $R^1$, p, q, and AO are the same as above.)

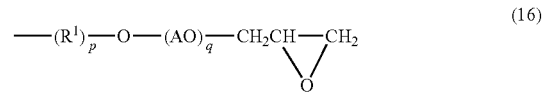

(wherein, $R^1$, p, q, and AO are the same as above.)

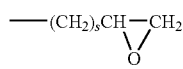 (17)

(wherein, s is a number of one or more.)

In formulae (12), (13), (15) and (16), $R^1$ and $R^2$ each are preferably an alkylene group having 1 to 12 carbons, particularly preferably having 1 to 8 carbons, and examples thereof include ethylene, propylene, trimethylene, tetramethylene, pentamethylene, hexamethylene, heptamethylene, and octamethylene groups, and the like. Among them, an ethylene, propylene or trimethylene group is more preferable, and an ethylene or trimethylene group is even more preferable, from the viewpoint of easiness in synthesis.

The substituents that may be present on $R^1$ and $R^2$ includes hydroxy, amino (having 1 to 22 carbons), imino (having 1 to 22 carbons) groups, and the like.

p is 0 or 1, and more preferably 1 from easiness in synthesis.

In formulae (12), (13), (15) and (16), AO is an alkyleneoxy or aryleneoxy group, preferably an ethyleneoxy, propyleneoxy, or phenyleneoxy group, and among them, an ethyleneoxy group is particularly preferable.

In formulae (12), (15), and (16), q is a number of 0 to 30, more preferably 0 to 5, and even more preferably 0 or 1 from the viewpoint of easiness in synthesis. If q is not 0, q AO's may be the same or different from each other, and if different, the mutual arrangement of these AO's may be in any sequential order including alternating, block, and other regular sequences or in a random manner.

In formula (13), r is a number of 0 to 30 and particularly preferably 0 to 5. r AO's may be the same or different from each other, and if different, the mutual arrangement of these AO's may be in any sequential order including alternating, block, and other regular sequences or in a random manner.

In the silicones having an amino or imino group of formula (14), $R^{13}$ is preferably, for example, an alkylene group having 1 to 12 carbons, and examples thereof include methylene, ethylene, propylene, trimethylene, tetramethylene, pentamethylene, hexamethylene, heptamethylene, octamethylene, and other groups.

Typical examples of the groups represented by formula (14) include 3-aminopropyl, N-(2-aminoethyl)-3-aminopropyl, N-(2-dimethylaminoethyl)-3-aminopropyl, N-alkylaminopropyl (having 1 to 22 carbons) groups, and the like. Among them, 3-aminopropyl, N-(2-aminoethyl)-3-aminopropyl and N-(2-dimethylaminoethyl)-3-aminopropyl groups are preferable and 3-aminopropyl group is more preferable from the viewpoint of availability.

The amine equivalence of the silicones having an amino or imino group (molecular weight per one mole of nitrogen atom) is preferably 300 to 50,000 g/mol, more preferably 300 to 10,000 g/mol, and even more preferably 300 to 5,000 g/mol, from the viewpoints of the modification ratio and the reaction efficiency. In addition, for improvement in the reaction efficiency, the viscosity thereof at 25° C. is preferably 10 to 1,000,000 mm$^2$/s and more preferably 20 to 10,000 mm$^2$/s. The viscosity of test samples is determined by using a type-B viscometer when the viscosity (25° C.) is below 100,000 mm$^2$/s, and a type-E viscometer when the viscosity (25° C.) is 100,000 mm$^2$/s or more.

In formula (17), s is preferably a number of 1 to 12.

A more preferable precursor silicone is a silicone wherein a group represented by the following formula (18) [hereinafter, referred to as group (18)] is connected to the silicon atom of the silicone.

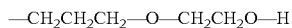 (18)

Preferable precursor silicones include silicones having a phenyl group substituted with at least one hydroxy group or with a polyoxyalkylene group having a hydroxy group at its end.

Preferable examples of the precursor silicones include silicones wherein a group represented by the following formula (19) [hereinafter, referred to as group (19)] is connected to the silicon atom of the silicone and silicones wherein a group represented by the following formula (20) [hereinafter, referred to as group (20)] is connected thereto.

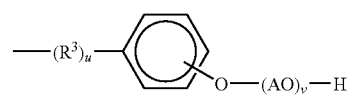 (19)

(wherein, $R^3$, u, v, and AO are the same as above.)

 (20)

(wherein, $R^4$, z, x, y, and AO are the same as above.)

In the groups (19) and (20), $R^3$ and $R^4$ each are preferably an alkylene group having 1 to 12 carbons, particularly preferably 1 to 8 carbons, and examples thereof include ethylene, propylene, trimethylene, tetramethylene, pentamethylene, hexamethylene, heptamethylene, octamethylene, and other groups. Among them, an ethylene, propylene or trimethylene group is more preferable and an ethylene or trimethylene group is even more preferable from the viewpoint of easiness in synthesis.

The substituents that may be present on $R^3$ and $R^4$ include hydroxy, amino (having 1 to 22 carbons), imino (having 1 to 22 carbons) groups, and the like. u and z each are 0 or 1, but more preferably 1 from the viewpoint of easiness in synthesis.

In the groups (19) and (20), AO is an oxyalkylene or oxyarylene group; an oxyethylene, oxypropylene, or oxyphenylene group is preferable; among them, an oxyethylene group is particularly preferable.

v, x and y each are a number of 0 to 30 and even more preferably 0 to 5, from the viewpoint of easiness of the starting reaction; If v, x, and y is not 0, v AO's, x AO's, and y AO's may be the same or different from each other, and if different, the mutual sequence of these AO's may be in any arrangement including alternating, block, and other regular sequences or in a random manner.

In the group (19), the positions of two substituents, the oxygen atom and the $(R^3)_u$ group (the silicon atom in silicone chain if u is 0), on the phenylene unit may be ortho, meta, or para to each other, or a mixture thereof. In the group (20), the position of either two or three substituents, the two oxygen atoms and the $(R^4)_z$ group (the silicon atom in the silicone chain when z is 0), on the phenylene unit may be ortho, meta, or para, or a mixture thereof.

Among the groups above, even more preferable group is a group represented by the following formula (21) [hereinafter, referred to as group (21)].

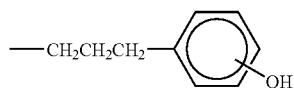

(21)

In the group (21), the position of two substituents, the hydroxy group and the trimethylene group, on the phenylene unit may be ortho, meta, or para, or a mixture thereof, but is more preferably ortho or para, or a mixture thereof from the viewpoint of easiness in synthesis.

In the precursor silicone, the group represented by formulae (12) to (21) described above may be present either at the side or the end of the silicone chain or a mixture thereof. Alternatively, one or more groups represented by formulae (12) to (21) above may be present therein. Several kinds of groups may be present therein.

In the precursor silicone, the substituents on the silicon atom other than the groups represented by formulae (12) to (21) above may be any group that is commonly used as a substituent of silicones, and preferable examples thereof include methyl, ethyl, butyl, octyl, vinyl, allyl, phenyl, methoxy, ethoxy, phenylpropyl, aminopropyl, dimethylaminopropyl, aminoethylaminopropyl, and polyoxyethylenepropyl groups, and the like. However, the substituent is particularly preferably a methyl group from the viewpoints of reduction in price and versatility, a phenyl group from the viewpoint of heat resistance, a butyl or octyl group from the viewpoint of improvement in hydrophobicity, an aminopropyl or dimethylaminopropyl group from the viewpoint of improvement in adsorptivity in acidic conditions, or particularly preferably an aminoethylaminopropyl group for improvement in hydrophilicity.

In the precursor silicone according to the invention, both-end-carbinol-modified polydimethylsiloxane, having two groups (18) at both ends of the straight-chain polydimethylsiloxane, and both-end-phenol-modified polydimethylsiloxane having two groups (21) at both ends of the straight-chain polydimethylsiloxane are very preferable, as they provide both-end-polyglycerol-(branched) modified silicones which easily form a higher-order structure binding to each other in water or other solvents, after the reaction of introducing branched polyglycerol chains. In addition, side chain multi-type carbinol- or phenol-modified polydimethylsiloxanes having three or more groups (18) or (21) on the side chains of the straight-chain polydimethylsiloxane preferably provide branched polyglycerol-modified silicones particularly superior in hydrophilicity and adsorptivity, after the reaction of introducing branched polyglycerol chains.

Examples of the acid catalysts for use in the reaction of glycidol with the precursor silicone include Lewis acids such as $BF_3OEt_2$, $HPF_6OEt_2$, $TiCl_4$, $SnCl_4$, sulfuric acid, $PhCOSbF_6$, perchloric acid, fluorosulfuric acid, trifluoroacetic acid, and trifluoromethanesulfonic acid (wherein, Et represents an ethyl group; and Ph, a phenyl group). Examples of the base catalysts for use in the reaction of glycidol with the precursor silicone include metal hydroxides such as LiOH, NaOH, KOH, and CsOH; alkaline metals such as Li, Na, K, and Cs, or the mercury amalgams thereof; metal alkoxides represented by formula $ROM^1$ (wherein, R: an alkyl group, preferably an alkyl group having 1 to 4 carbons; and $M^1$: alkaline metal); metal hydrides of alkaline or alkali earth metals; organometallic compounds such as n-butyl lithium, t-butyl lithium, potassium pentadienide, potassium naphthalene, and Grignard reagents; and the like. Among them, preferable are alkaline metals, metal hydroxides, metal alkoxides, and organometallic compounds, as they are highly reactive, and further among them, K, KOH, CsOH, potassium hydride, potassium methoxide, potassium isopropoxide, and potassium butoxide are particularly preferable as a catalyst that is superior both in convenience and high activity.

The amount of these catalysts used may be suitably determined according to the polymerization activity of the catalyst used, the total amount and the concentration of reactive functional groups such as hydroxy (including a hydroxy group on the phenyl group and/or at the end of the polyoxyalkylene group bound to the phenyl group), carboxy, amino, imino, mercapto and epoxy groups in the precursor silicone, and the like; but the amount thereof is preferably 0.001 to 2 molar equivalences, more preferably 0.01 to 2.0 molar equivalences, even more preferably 0.01 to 1.0 molar equivalences, and even more preferably 0.03 to 0.3 molar equivalences in the case of an acid catalyst, and preferably 0.01 to 2 molar equivalences, more preferably 0.03 to 1.0 molar equivalences, and even more preferably 0.05 to 0.8 molar equivalences in the case of a base catalyst with respect to the total molar equivalence of these functional groups. In the ranges above, the reaction progresses smoothly in high yield with low side reactions, providing branched polyglycerol-modified silicones with high purity. The side reactions that may proceed include cyclization of glycerol into macrocycles, decomposition of silicones, generation of glycerol polymers not bound to silicones or bound to the shorter silicone chains as a decomposition product, and the like.

Use of a metal hydroxide or metal alkoxide, among the base catalysts above, leads to the generation of water or alcohol by the reaction between the catalyst and the precursor silicone. It is preferable to reduce the amount of water and/or alcohol as much as possible, as they possibly cause the side reactions above. So, in the case of using these catalysts, water or alcohol is preferably removed prior to the addition of glycidol to the mixture of these catalysts and the precursor silicone. For removal of water or alcohol, the mixture may be heated to a temperature of the boiling point thereof or more or subjected to a dehydration or dealcoholization processing, for example, under reduced pressure after the catalysts are added to the precursor silicone.

The glycidol for use in the invention may be a commercial product, but is more preferably purified, for example, by dehydration, deoxygenation, and subsequent distillation at 50° C. or lower under an inert gas stream and a reduced pressure. Glycidol is preferably purified immediately before use, but may be stored at −20° C. or lower under a dry inert gas atmosphere if needed.

The amount of glycidol used may be determined suitably according to the desirable amount of polyglycerol group introduced. It is possible to control the average number of glycerol units per a branched polyglycerol chain, by properly selecting the mole number of glycidol with respect to the total mole number of the reactive functional group, such as hydroxy groups (including a hydroxy group present on the phenyl group and/or at the end of the polyoxyalkylene group bound to the phenyl group), carboxy group, amino group, imino group, mercapto group and epoxy group, on the precursor silicone. The amount of glycidol is 0.1 molar equivalence or more, preferably 3 molar equivalences or more, more preferably 3 to 200 molar equivalences, even more preferably 3 to 100 molar equivalences, even more preferably 3 to 50 molar equivalences, and still more preferably 3 to 20 molar equivalences with respect to 1 molar equivalence of the reactive functional group. On the other hand, it is possible to control the content of the branched polyglycerol chains in the branched polyglycerol-modified silicone, i.e., hydrophilicity/hydrophobicity ratio, by properly selecting the mole number of the glycidol used with respect to the total mole number of the silicon atoms in the precursor silicone. The amount of glycidol is preferably 0.001 to 50 molar equivalences, more preferably 0.05 to 10 molar equivalences, even more preferably 0.1 to 3 molar equivalences, and even more preferably 0.15 to 1 molar equivalence, with respect to 1 molar equivalence of silicon atom. In this range, it is possible to produce branched polyglycerol-modified silicones superior in affinity to hydrophilic solvents and higher in residual adsorptivity rate on various media, skin, hair, and fabrics.

For production of the branched polyglycerol-modified silicones according to the invention, glycidol is preferably added and polymerized after the addition and the mixing of the acid or base catalyst to the precursor silicone. The polymerization temperature may be selected arbitrarily according to the polymerization activity of the catalyst used, the molecular weight of precursor silicone, the concentration of the reactive functional groups, such as hydroxy groups (including a hydroxy group on the phenyl group and/or at the end of the polyoxyalkylene group bound to the phenyl group), carboxy, amino, imino, mercapto and epoxy groups on the precursor silicone, and the like, but is preferably −78 to 220° C. and more preferably −30 to 150° C. The polymerization temperature is preferably −30 to 70° C. when an acid catalyst or an organometallic catalyst described above is used, while the polymerization temperature is preferably 30 to 130° C. and more preferably 60 to 110° C. when a base catalyst other than organometallic catalysts is used.

Glycidol is preferably added, while being stirred, dropwise or intermittently with smaller portions, not adding by all at once. The period of the dropwise addition depends on the amounts of glycidol and the catalyst used and the polymerization activity of the catalyst, but is preferably 0.25 to 24 hours and even more preferably 1 to 12 hours. Branched polyglycerol-modified silicones with narrower in composition distribution can be produced if the period is elongated. The reaction mixture may be aged for 0.1 to 3 hours after the completion of addition of glycidol.

The graft polymerization reaction of glycidol with the precursor silicone according to the invention is preferably carried out under an atmosphere of an inert gas such as nitrogen, argon, or the like, or under deoxygenated reduced pressure, for improving the polymerization activity.

The graft polymerization reaction of glycidol with the precursor silicone according to the invention is preferably carried out in the absence of solvents from the viewpoint of the convenience in commercial production, but may be conducted in the presence of a suitable solvent, if the reaction system becomes extremely highly viscous, solid, or a heterogeneous slurry mixture, depending on the composition of the precursor silicone, catalyst species, the amount of the catalyst, and the amount of glycidol added. Examples of the solvents include amphiphilic solvents such as tetrahydrofuran (THF), dioxane, and ethylene glycol dimethylether; hydrocarbon solvents including aliphatic hydrocarbons such as hexane, heptane, cyclohexane, methylcyclohexane, isooctane, and hydrogenated triisobutylene, and aromatic hydrocarbons such as benzene, toluene, xylene, and ethylbenzene, and the like; silicone solvents such as octamethylcyclotetrasiloxane, and decamethylcyclopentasiloxane; and the like. The solvent may be used as previously added to the precursor silicone or part or all of the solvent may be used as a diluent solvent for glycidol. If used, the solvent is used in an amount of 0.01 to 1000 parts by weight, preferably 0.1 to 100 parts by weight, and even more preferably 0.2 to 20 parts by weight with respect to 1 part by weight of precursor silicone. These solvents are normally preferred to use with being dried and deoxygenated thoroughly.

In production of the branched polyglycerol-modified silicones according to the invention, ethylene oxide and/or propylene oxide may be copolymerized during addition/graft polymerization of glycidol, if the copolymerizaton does not significantly impair the characteristics of the branched polyglycerol-modified silicone according to the invention, i.e., the silicone-like characteristics, hydrophilic property, and high adsorptivity of the resulting modified silicone. Ethylene oxide and/or propylene oxide may be blended with glycidol before addition; glycidol may be added after addition of ethylene oxide and/or propylene oxide; alternatively, ethylene oxide and/or propylene oxide may be added after addition of glycidol. The amount of ethylene oxide and/or propylene oxide used is 0.001 to 0.5 molar equivalence and preferably 0.02 to 0.2 molar equivalence with respect to 1 molar equivalence of glycidol.

[Cosmetics]

The content of the branched polyglycerol-modified silicone according to the invention in cosmetics of the invention may be determined according to the applications of the cosmetics and thus is not particularly limited, but preferably is from 0.001 to 50%, more preferably 0.01 to 30%, even more preferably 0.1 to 10%, and even more preferably 0.5 to 10%, by weight of the cosmetics.

The form of cosmetic according to the invention is not particularly limited, and thus the cosmetic may be water-in-oil or oil-in-water type emulsified cosmetics, oil-based cosmetics, spray cosmetics, stick-like cosmetics, aqueous cosmetics, sheet-like cosmetics, gel cosmetics, or the like. The kind of cosmetic according to the invention is also not particularly limited, and examples thereof include skin cosmetics such as a facial mask, foundation, lipstick, lotion, cold cream, hand cream, skin cleanser, emollient, nourishing cosmetics, astringent, whitening cosmetics, crease proof cosmetics, antiaging cosmetics, cleansing cosmetics, antiperspirant, and deodorant; and hair cosmetics such as shampoo, rinse, treatment, hair dressing, and hair tonic.

The cosmetics according to the invention may contain alcohols. Examples of the alcohols include monohydric or polyhydric alcohols having 1 to 6 carbons such as ethanol, glycerol, 1,3-butylene glycol, propyleneglycol, sorbitol, and among them, a monohydric alcohol, particularly ethanol, is preferable. The amount of alcohol blended in the cosmetics according to the invention is preferably 5 to 30% and more preferably 2 to 50 times by weight higher than that of the branched polyglycerol-modified silicone according to the invention.

The cosmetics according to the invention may also contain other ingredients commonly used as cosmetic ingredients in the range suitably determined according to the form and kind of the cosmetics that does not impair the advantageous effects of the invention. Examples of these cosmetic ingredients include extender pigments such as mica, talc, sericite, kaolin, nylon powder, polymethylsilsesquioxane, and barium sulfate; inorganic pigments such as titanium oxide, zinc white, and iron oxide; particles obtained from the ingredients above by a surface hydrophobilization treatment such as silicone treatment, metallic soap treatment, or N-acylglutamic acid treatment; hydrocarbons such as solid or liquid paraffin, microcrystalline wax, vaseline, ceresin, ozokerite, and montan wax; vegetable/animal oils and waxes such as olive oil, earth wax, carnauba wax, lanolin, and whale wax; fatty acids or the esters thereof such as stearic acid, palmitic acid, oleic acid, glycerol monostearic ester, glycerol distearic ester, glycerol monooleic ester, isopropyl myristic ester, isopropyl stearic ester, and butyl stearic ester; higher alcohols such as cetyl alcohol, stearyl alcohol, palmityl alcohol, and hexyldodecyl alcohol; adsorbants and thickeners such as cationized cellulose, carboxy betaine polymer, and cationized silicone; polyvalent alcohols having a moisturizing action such as glycol and sorbitol; medicinal ingredients such as whitening agent, analgesic antiphlogistic agent, antipruitic agent, bacteriocidal disinfectant, astringent, emollient, and hormone drug; water; surfactants; W/O or O/W emulsifiers; emulsifiers for silicone oils such as polyether-modified silicones, polyether, alkyl modified silicones, and glyceryl ether modified silicones; and thickeners such as methylcellulose, ethylcellulose, carboxymethylcellulose, polyacrylic acid, tragacanth, agar, and gelatin; and in addition, emulsion stabilizers, chelate agents, UV-protecting agents, ph adjusters, antiseptics, dyes, flavors, and the like.

[Other Applications of Branched Polyglycerol-Modified Silicones]

In addition to cosmetics, the branched polyglycerol-modified silicone according to the invention may be used in various other industrial fields where conventional silicone compounds have been used, as a more preferable silicone compound, i.e., as a silicone compound drastically improved in hydrophilicity, as a modified hydrophilic silicone compound improved in coating properties and the adsorptivity onto various media, or as a modified silicone compound retaining various properties inherent in silicones. In addition, they may also be used in some industrial fields where conventional silicone compounds were not used as a preferable material that would be able to solve the problems in those fields.

The shape of the branched polyglycerol-modified silicone according to the invention when it is used in the industrial fields other than cosmetics is not particularly limited, and the modified silicone may be shipped in any shape or form, and examples thereof include pure material; solution, dispersion, and oil-based gel such as silicone and/or alcohol; aqueous solution or dispersion, emulsion containing other oils, and water-containing gel; wax; other solid materials blended or impregnated therewith; and the like.

In addition to the application to cosmetics, applications of the branched polyglycerol-modified silicone according to the invention include, but is not particularly limited to, additives for varnishes and paints superior in heat-resisting/weather-resisting/electrical properties, polyol ingredients, foam stabilizers and modifiers for various urethanes and expanding materials, lubricants and releasing agents, antifoamers, greases and oil compounds, oils for insulation, glazing, water repellency, heating and cooling media, lubrication, and the like, modifiers, additives, and surface finishing agents for rubbers and resins, ingredients, modifiers, and precursors for silane coupling agents, coating and sealing materials for construction and lining, protective materials for optical fibers and electric wires, releasing agents and buffer agents, and the like.

The branched polyglycerol-modified silicone according to the invention has a solubility in hydrophilic solvents not significantly different from that of a straight-chain polyglycerol-modified silicone, but exhibits a higher adsorptivity onto skin, fabrics, and the like in hydrophilic solvents. It is presumably because the branched polyglycerol-modified silicone according to the invention has a smaller molecular radius of the gyration and thus the degree of dynamic molecular mobility is extremely restricted and when one terminal hydroxy group among many hydroxy groups on the this modified-silicone is once bound to the medium surface via a hydrogen bond, the neighboring hydroxy groups localized and restricted in motion are adsorbed in succession, making the entire molecule function as a powerful cluster of adsorptive groups.

In particular, branched polyglycerol-modified silicones with narrower composition distribution, that exhibit the inherent properties more drastically, can be produced when the modified silicone has an oxyphenylene group as the connecting group between the silicone chain and the branched polyglycerol chain. In addition, in the method of producing a polyglycerol-modified silicone according to the invention, when the precursor silicone has a group having a phenol as the reactive functional group, the reaction of producing the branched polyglycerol-modified silicone proceeds almost quantitatively in very high yield without other side reactions such as decomposition of silicone chains and the like, and provides branched polyglycerol-modified silicones with high purity and narrower composition distribution. In this manner, the process of production according to the invention is an extremely preferable method.

EXAMPLES

The following examples further describe and demonstrate embodiments of the present invention. The examples are given solely for the purpose of illustration and are not to be construed as limitations of the present invention.

Commercially available precursor silicone, potassium methoxide-methanol solution, and potassium were used as they are in the EXAMPLES below. Glycidol was purified by distillation in the presence of calcium hydride at 40 to 42° C. under reduced pressure and an argon environment just prior to use.

The chemical shifts in the $^1$H-NMR spectra of the branched polyglycerol-modified silicones obtained in the EXAMPLES below vary slight according to the solvent used, but are almost as follows:

0.0-0.2 ppm: Si—C$\underline{\text{H}}_3$
0.6-0.7 ppm: Si—C$\underline{\text{H}}_2$—CH$_2$— (4H)
1.5-1.7 ppm: Si—C$\underline{\text{H}}_2$—CH$_2$— (4H)
2.4-2.7 ppm: Si—CH$_2$—C$\underline{\text{H}}_2$—CH$_2$— (4H)
3.3-4.0 ppm: H on branched polyglycerol chain (5H×Number of glycerol groups excluding terminal hydroxy groups)
6.7-7.2 ppm: Phenol (8H)

The peaks in $^{13}$C-NMR spectra derived from the carbons in the groups (1) to (4) constituting the branched polyglycerol chains are assigned with reference to the values described in Macromolecules, 1999, 32, 4240.

Example 1

Branched Polyglycerol-Modified Silicone A (Having —CH$_2$CH$_2$CH$_2$—O—CH$_2$CH$_2$O— as the Connecting Group)

Figure 2:
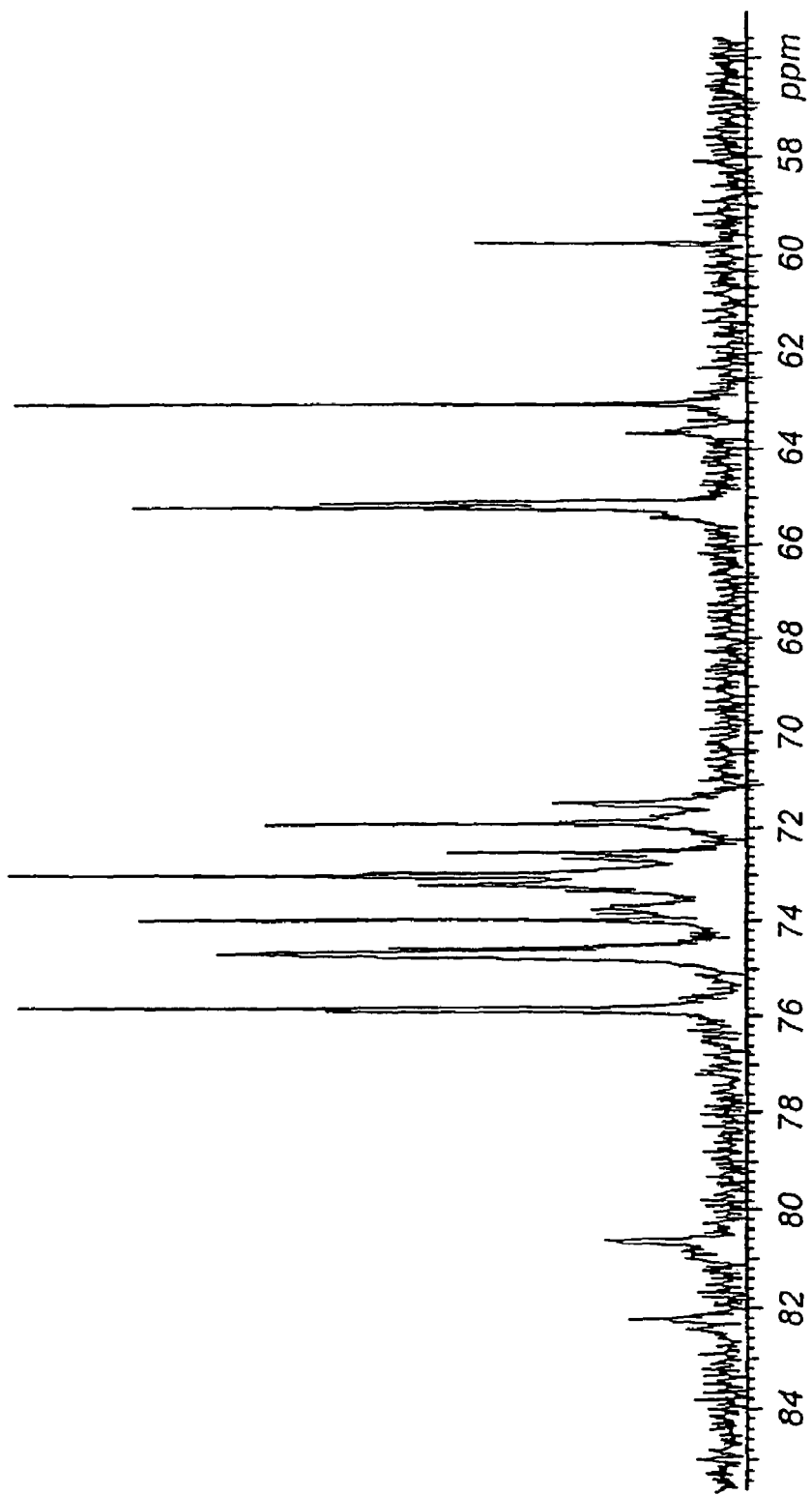
FIG. 2 is a $^{13}$C-NMR spectrum of the branched polyglycerol-modified silicone A obtained in Example 1.

Into a flask containing 187 g of carbinol-modified silicone XF42-B0970 manufactured by GE Toshiba Silicones [both ends modified; hydroxy equivalence: 60 mg-KOH/g (average molecular weight: equivalent to 1,870)], 42.1 g of potassium methoxide (30% methanol solution) was added, and the mixture was heated to 60° C. under reduced pressure while being stirred to remove entirely methanol, to give potassium salt of a carbinol-modified silicone as a yellow oil. To the modified silicone heated to 95° C., 74.1 g (5 equivalences) of glycidol was added by using a metering pump over a period of 5 hours while the mixture was stirred vigorously under an argon atmosphere. After heating and stirring additionally for 20 minutes, the mixture was allowed to cool to room temperature and added with 600 mL of ethanol, to give a pale yellow solution. After addition of 34.6 g of citric acid, the mixture was stirred and the resulting salt precipitated was removed by filtration. The filtrate was concentrated (when a small amount of polyglycerol-rich derivative was formed, it should be removed) to give branched polyglycerol-modified silicone A as a pale yellow oil. Yield: 95%. $^1$H-NMR spectrum of branched polyglycerol-modified silicone A (methanol-d$_4$ solution) is shown in FIG. 1, and $^{13}$C-NMR spectrum (methanol-d$_4$ solution) in FIG. 2. Results of assignment of the peaks in the $^1$H-NMR spectrum and the methine peak of group (1) in the $^{13}$C-NMR spectrum are as follows:

$^1$H-NMR spectrum
0.05-0.25 ppm (Si—CH$_3$)
0.6-0.7 ppm (4H, Si—$\overline{\text{CH}}_2$—CH$_2$—)
1.6-1.8 ppm (4H, Si—C$\overline{\text{H}}_2$—CH$_2$—)
3.35-4.0 ppm (12H, Si—$\overline{\text{CH}}_2$—CH$_2$—CH$_2$—O—CH$_2$—CH$_2$O, H in branched polyglycerol chain)
$^{13}$C-NMR spectrum 78.0-8.10 ppm 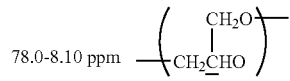

Analysis of the $^{13}$C-NMR spectrum confirmed that branched polyglycerol-modified silicone A is a branched polyglycerol-modified silicone having the group (1). In addition, analysis of the $^1$H-NMR spectrum revealed that modified silicone A has an average number of glycerol groups (G) of 9.8 (4.9 at each end), an average number of silicon atoms (Si) of 22, and a G/Si ratio of 0.45, while GPC analysis [column: KF-804L (×2), aliphatic amine/chloroform solution, 40° C., as polystyrene] revealed that the modified silicone A had a number-average molecular weight (M$_n$) of 2,600.

Example 2

Branched Polyglycerol-Modified Silicone B (Having —CH$_2$CH$_2$CH$_2$—O—CH$_2$CH$_2$O as the Connecting Group)

To a flask containing 181 g of carbinol-modified silicone KF-6001 manufactured by Shin-Etsu Chemical Co. Ltd., [both ends modified, hydroxy equivalence: 62 mg-KOH/g (average molecular weight: equivalent to 1,810)], 46.7 g of potassium methoxide (30% methanol solution) was added, and the resulting mixture was heated to 60° C. while being stirred under reduced pressure to remove entirely methanol, to give a potassium salt of carbinol-modified silicone as a pale yellow oil. To the modified silicone heated to 95° C., 177.8 g (12 equivalences) of glycidol was added by using a metering pump over a period of 8 hours while the mixture was stirred vigorously under an argon atmosphere. After heating and stirring additionally for 20 minutes, the mixture was allowed to cool to room temperature, to give a turbid milky white paste-like composition. After addition of 800 mL of ethanol and removal of potassium by a cation-exchange resin, the solution was concentrated to give branched polyglycerol-modified silicone B as a pale yellow viscous oil. Yield: 92%. $^{13}$C-NMR spectrum analysis confirmed that modified silicone B is a branched polyglycerol-modified silicone having the group (1). In addition, analysis of the $^1$H-NMR spectrum revealed that modified silicone B had an average number of glycerol groups (G) of 23.6 (11.8 at each end), an average number of silicon atoms (Si) of 22, and a G/Si ratio of 1.07, while GPC analysis (column: G4000PWXL+G2500PWXL, acetonitrile/phosphate buffer solution, 40° C., as polyethylene glycol) revealed that modified silicone B had a number-average molecular weight (M$_n$) of 3,590.

Example 3

Branched Polyglycerol-Modified Silicone C (Having —CH$_2$CH$_2$CH$_2$—O—CH$_2$CH$_2$O— as the Connecting Group)

Figure 3:
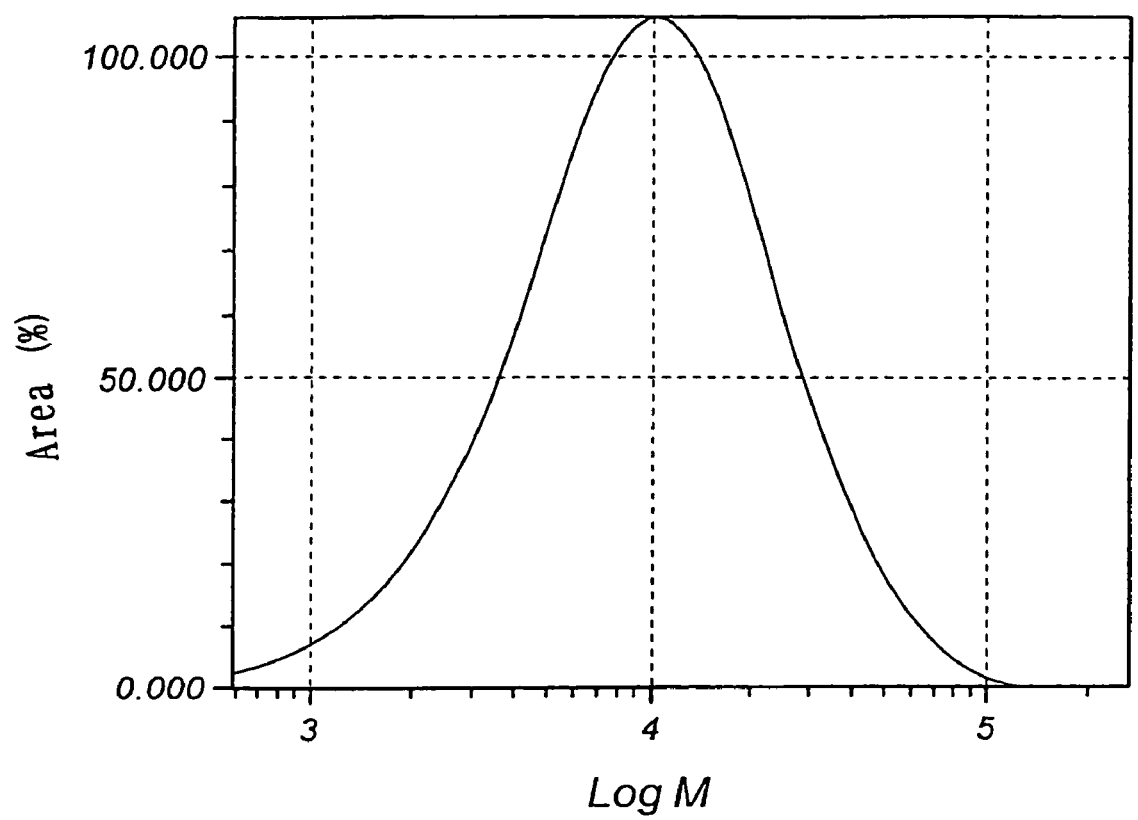
FIG. 3 is a chart illustrating the GPC results of the branched polyglycerol-modified silicone C obtained in Example 3.

Into a flask containing 200 g of carbinol-modified silicone KF-6003 manufactured by Shin-Etsu Chemical Co. Ltd. [both ends modified, hydroxy equivalence: 22 mg-KOH/g (average molecular weight: equivalent to 5,100)], 2.45 g of finely cut potassium was added under an argon atmosphere, and the resulting mixture was stirred at 60° C. until the potassium granules disappeared, to give a potassium salt of carbinol-modified silicone as an oil. To the modified silicone heated to 95° C., 29.1 g (5 equivalences) of glycidol was added over a period of 5 hours while the mixture was stirred vigorously under an argon atmosphere. After heating and stirring additionally for 10 minutes, the mixture was allowed to cool to 30° C. and added with 800 mL of ethanol. After removal of potassium ion by using a cation-exchange resin, the solution was concentrated, to give branched polyglycerol-modified silicone C as a pale yellow viscous oil. Yield: 88%. $^{13}$C-NMR spectrum analysis confirmed that modified silicone C is a branched polyglycerol-modified silicone having the group (1). In addition, analysis of the $^1$H-NMR spectrum revealed that modified silicone C had an average number of glycerol groups (G) of 10.2 (5.1 at each end) and an average number of silicon atoms (Si) of 69, and a G/Si ratio of 0.15. Results of the GPC of branched polyglycerol-modified silicone C (solvent: chloroform) are shown in FIG. 3. The GPC analysis (column: KF-804L (×2), aliphatic amine/chloroform solution, 40° C., as polystyrene) showed that modified silicone C had a number-average molecular weight (M$_n$) of 6,280.

Example 4

Branched Polyglycerol-Modified Silicone D (Having —CH$_2$—O—CH$_2$CH$_2$O— as the Connecting Group)

Into a flask containing 300 g of epoxy modified silicone SF8411 manufactured by Dow Corning Toray Silicone Co. Ltd. (glycidyl-modified on side chain, epoxy equivalence: 3,000), 23.4 g of potassium methoxide (30% methanol solution) was added, and the mixture was stirred at 80° C. for 30 minutes. Then, methanol was all distilled off at 60° C. under reduced pressure, to give a potassium salt of silicone as a pale yellow oil. To the oil heated to 95° C., 111.1 g of glycidol (15 equivalence) was added gradually by using a metering pump over a period of 8 hours while the mixture was vigorously stirred under an argon atmosphere. After heating and stirring additionally for 20 minutes, the mixture was allowed to cool to room temperature, to give a turbid milky white paste. After addition of 800 mL of ethanol and removal of potassium by using a cation-exchange resin, the solution was concentrated, to give branched polyglycerol-modified silicone D as a pale yellow viscous oil. Yield: 87%. $^{13}$C-NMR spectrum analysis confirmed that modified silicone D is a branched polyglycerol-modified silicone having the group (1). In addition, analysis of the $^1$H-NMR spectrum revealed that modified silicone D had an average number of glycerol groups (G) of 13.6 and a G/Si ratio of 0.35.

Example 5

Branched Polyglycerol-Modified Silicone E (Having —CH$_2$—O—CH$_2$CH$_2$O— as the Connecting Group)

Into a flask containing 200 g of polyether-modified silicone SH3775M manufactured by Dow Corning Toray Silicone Co. Ltd. (polyether-modified on side chain; hydrophilic-lipophilic balance, HLB: 5), 14.2 g of potassium methoxide (30% methanol solution) was added, and the mixture was stirred at 80° C. for 30 minutes. Then, methanol was all distilled off at 60° C. under reduced pressure, to give a potassium salt of silicone as a slightly turbid pale yellow slurry. To the modified silicone heated to 95° C., 28.1 g of glycidol was added by using a metering pump over a period of 5 hours while the mixture was stirred vigorously under an argon atmosphere. After heating and stirring additionally for 10 minutes, the mixture was allowed to cool to room temperature to give a turbid milky white paste. After addition of 800 mL of ethanol and removal of potassium by a cation-exchange resin, the solution was concentrated to give a branched polyglycerol-modified silicone E as a pale yellow viscous oil. Yield: 87%. $^{13}$C-NMR spectrum analysis confirmed that the modified silicone is a branched polyglycerol-modified silicone having the group (1). After addition of 300 mL of hexane, the mixture was stirred and then left standing. The soluble part was separated and concentrated to give branched polyglycerol-modified silicone E. Analysis of the $^1$H-NMR spectrum revealed that modified silicone E had an average number of ethylene oxide groups of 16.8, an average number of glycerol groups (G) of 5.1, and a G/Si ratio of 0.61. GPC analysis [column: G4000HXL+G2000HXL, THF solution (50 mmol/L acetic acid), 40° C., as polystyrene] revealed that the modified silicone E had a number-average molecular weight ($M_n$) of 1,700.

Example 6

Branched Polyglycerol-Modified Silicone F (Having —CH$_2$—O—CH$_2$CH$_2$O— as the Connecting Group)

Into a flask containing 200 g of carbinol-modified silicone KF6003 manufactured by Shin-Etsu Chemical Co. Ltd., 14.7 g of potassium methoxide (30% methanol solution) was added, and the mixture was stirred at 80° C. for 30 minutes. After methanol was all distilled off at 60° C. under reduced pressure, 100 mL of distilled pure dioxane was added, to give a pale yellow solution of a potassium salt of silicone. To the modified silicone heated to 95° C., 40.7 g (7 equivalences) of glycidol was added over a period of 6 hours by using a metering pump while the mixture was stirred vigorously under an argon stream. After heating and stirring additionally for 10 minutes, the mixture was allowed to cool to 30° C. and added with 400 mL of ethanol. After separation of insoluble solid matters and removal of potassium by using a cation-exchange resin, the solution was concentrated to give branched polyglycerol-modified silicone F as a turbid yellowish white paste. Yield: 85%. $^{13}$C-NMR spectrum analysis confirmed that modified silicone F is a branched polyglycerol-modified silicone having the group (1). Analysis of the $^1$H-NMR spectrum revealed that modified silicone F had an average number of glycerol groups (G) of 13.5 and a G/S ratio of 0.39.

Example 7

Branched Polyglycerol-Modified Silicone G (Having —CH$_2$—O—CH$_2$CH$_2$O— as the Connecting Group)

Into a flask containing 200 g of carbinol-modified silicone BY16-201 manufactured by Dow Corning Toray Silicone Co. Ltd. [both ends modified, hydroxy equivalence: 950 (average molecular weight: equivalent to 1,900)] cooled in an ice bath under an argon atmosphere, 1.47 g of titanium tetrachloride was added gradually over a period of 10 minutes. The slightly turbid pale yellow solution thus obtained was left standing at 45° C. for 30 minutes, to become colorless. To the solution heated to 95° C., 27.3 g (5 equivalences) of glycidol was added by using a metering pump over a period of 5 hours while the mixture was stirred vigorously under an argon stream. After heating and stirring additionally for 10 minutes, the mixture was allowed to cool to room temperature and added with 400 mL of ethanol, and insoluble solid matters including titanium oxides were filtered. The filtrated was concentrated, to give branched polyglycerol-modified silicone G as a turbid yellowish white paste. Yield: 85%. Analysis of the $^{13}$C-NMR spectrum confirmed that modified silicone G is a branched polyglycerol-modified silicone having the group (1). Analysis of the $^1$H-NMR spectrum revealed that modified silicone G had an average number of glycerol groups (G) of 9.5 and a G/Si ratio of 0.44.

Example 8

Branched Polyglycerol-Modified Silicone H (Having —CH$_2$—O—CH$_2$CH$_2$O— as the Connecting Group)

Into a flask containing 150 g of carbinol-modified silicone KF6003 manufactured by Shin-Etsu Chemical Co. Ltd. cooled in an ice bath under an argon atmosphere, 0.417 g of BF$_3$OEt$_2$ was added dropwise over 10 minutes. To the slightly turbid colorless viscous solution thus obtained, 21.8 g of glycidol (5 equivalences) was added by using a metering pump at 50° C. over a period of 4 hours while the mixture was stirred vigorously. After heating and stirring additionally for 10 minutes, the mixture was allowed to cool to room temperature and added with 200 mL of ethanol. The insoluble solid matters are separated. The solution was concentrated to give branched polyglycerol-modified silicone H as a colorless oil. Yield: 82%. Analysis of the $^{13}$C-NMR spectrum confirmed that modified silicone H is a branched polyglycerol-modified silicone having the group (1). Analysis of the $^1$-HNM spectrum revealed that modified silicone H had an average number of glycerol groups (G) of 7.6 and a G/Si ratio of 0.12.

Example 9

Branched Polyglycerol-Modified Silicone I (Connecting Group: —CH$_2$CH$_2$CH$_2$—C$_6$H$_4$—O—)

Figure 4:
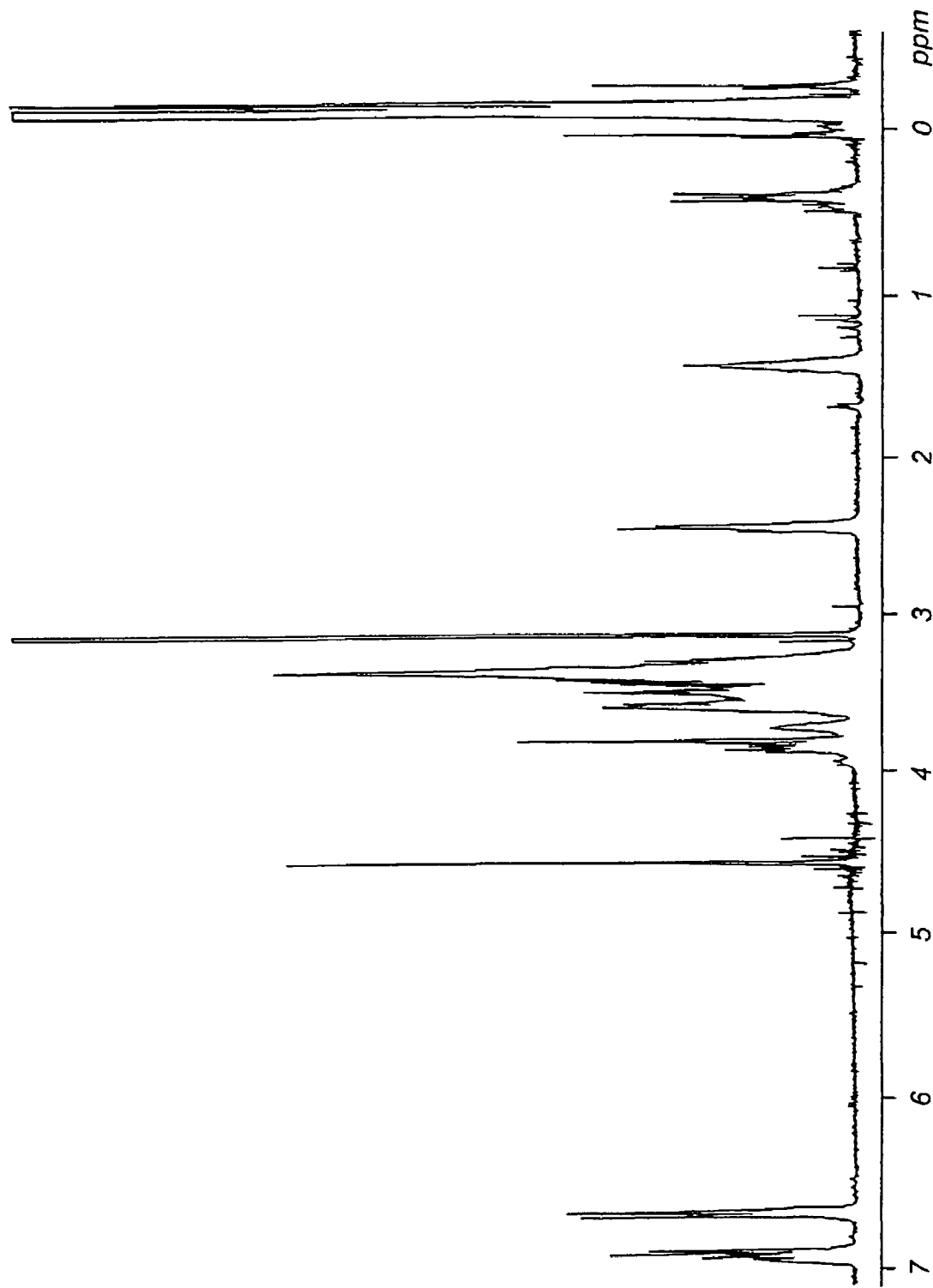
FIG. 4 is a $^1$H-NMR spectrum of the branched polyglycerol-modified silicone I obtained in Example 9.
Figure 5:
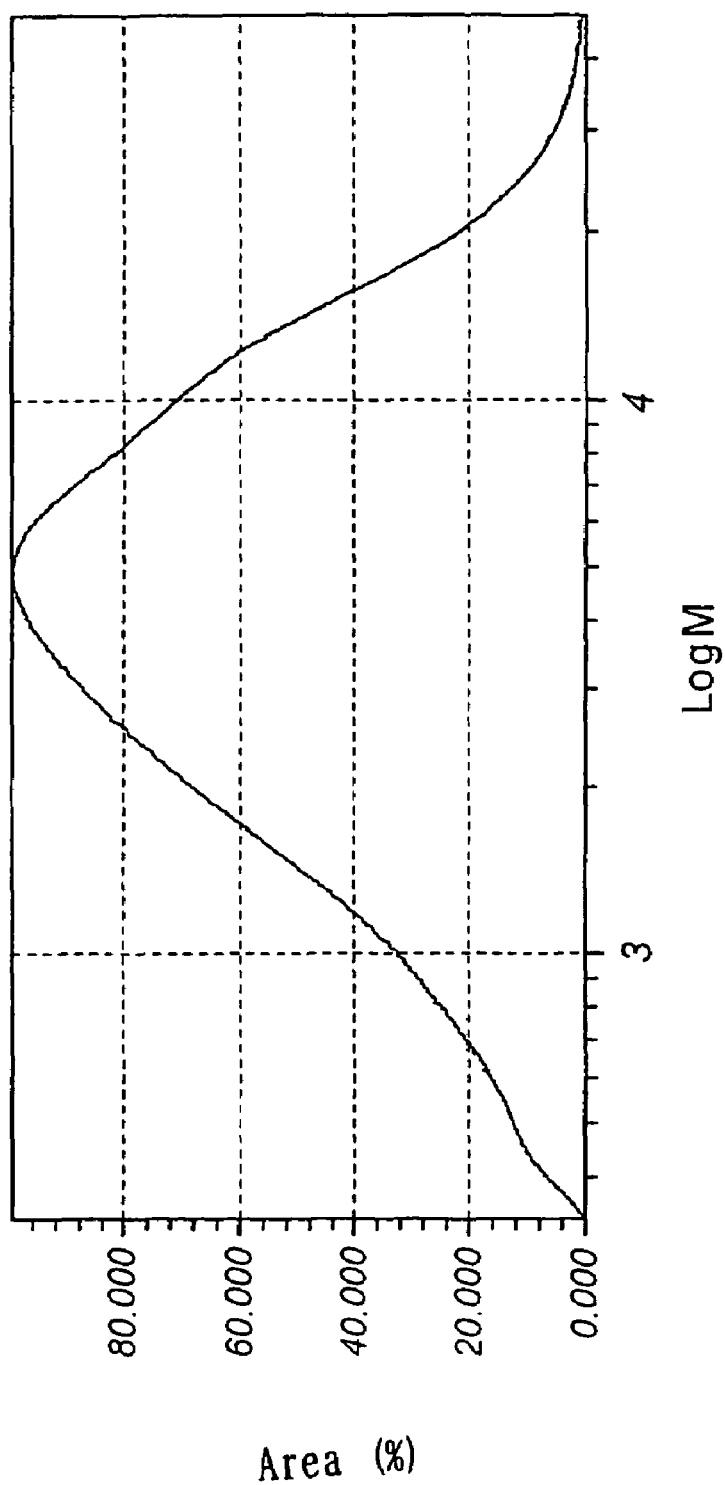
FIG. 5 is a chart illustrating the GPC results of branched polyglycerol-modified silicone I obtained in Example 9.

Into a flask containing 150 g of phenol-modified silicone BY16-752 manufactured by Dow Corning Toray Silicone Co. Ltd. [both ends modified, specific density: 0.99 g/mL, viscosity: 110 cSt, hydroxy group equivalence: 1,500 (average molecular weight: equivalent to 3,000), GPC (column: G4000HXL+G2000HXL (manufactured by Tosoh Corporation), THF solution (50 mmol/L acetic acid added), 40° C., as polystyrene], measured number-average molecular weight ($M_n$): 2,340, measured weight-average molecular weight ($M_w$): 4,780], 5.61 g of 30% potassium methoxide methanol solution was added, and the mixture was heated to 60° C. while being stirred under reduced pressure to distill methanol off completely, to give a potassium salt of phenol-modified silicone as a yellow oil. To the modified silicone heated to 95° C., 31.0 g (4.2 equivalents) of glycidol was added over a period of 3.5 hours while the mixture was stirred vigorously under an argon atmosphere. After heating and stirring additionally for 20 minutes, the mixture was allowed to cool to room temperature, to give a yellowish white solid product. Although the polyglycerol-modified silicone obtained might be used as it was, it can be purified by removing potassium present, for example, by adding 500 mL of ethanol, removing potassium by using a cation-exchange resin, and concentrating the resulting solution. In this manner, branched polyglycerol-modified silicone I was obtained as a pale yellow oil. Yield: 98%. Analysis of the $^{13}$C-NMR confirmed that modified silicone I was a branched polyglycerol-modified silicone having the group (1). In addition, analysis of the $^1$H-NMR revealed that modified silicone I had an average number of glycerol groups (G) of 8.6 (4.3 at each end), an average number of silicon atoms (Si) of 31.9, and a G/Si ratio of 0.27. GPC analysis [column: G4000HXL+G2000HXL, THF solution (50 mmol/L acetic acid added), 40° C., as polystyrene] showed that modified silicone I had an $M_n$ of 2,650 and an $M_w$ of 5,820. $^1$H-NMR spectrum of branched polyglycerol-modified silicone I obtained [methanol-$d_4$/chloroform-d (4/1) solution] is shown in FIG. 4, and the results of GPC, in FIG. 5.

Example 10

Branched Polyglycerol-Modified Silicone J (Connecting Group: —CH$_2$CH$_2$CH$_2$—C$_6$H$_4$—O—)

Into a flask containing 1,000 g of phenol-modified silicone BY16-752 manufactured by Dow Corning Toray Silicone Co. Ltd., 46.8 g of 30% potassium methoxide methanol solution was added, and the mixture was heated to 60° C. under reduced pressure while being stirred to distill methanol off completely, to give a potassium salt of phenol-modified silicone as a yellow oil. To the modified silicone heated to 95° C., 148.1 g (3.0 equivalents) of glycidol was added by using a metering pump over a period of 4.3 hours while the mixture was stirred vigorously under an argon atmosphere. After heating and stirring additionally for 10 minutes, the mixture was allowed to cool to the room temperature to give a pale yellow paste product. Although the polyglycerol-modified silicone obtained might be used as it was, it can be purified by the cation-exchange resin treatment described in Example 9 to remove the coexisting potassium ion. In this manner, branched polyglycerol-modified silicone J was obtained as a pale yellow oil. Yield: 99.7%. Analysis of the $^{13}$C-NMR confirmed that modified silicone J was a branched polyglycerol-modified silicone having the group (1). In addition, analysis of the $^1$H-NMR revealed that modified silicone J had a G of 6.2 (3.1 at each end), an Si of 32.3, and a G/Si ratio of 0.19.

To 1,145 g of branched polyglycerol-modified silicone J thus obtained, 400 mL of ethanol was added. High-speed centrifugation (2×10$^4$ G, 60 minutes, 20° C.) of the mixture lead to phase separation. The upper phase was concentrated, to give an easily soluble hydrophilic component as a yellow oil (438 g; branched polyglycerol-modified silicone J-1). On the other hand, concentration of the lower phase provided a hardly-soluble hydrophobic component as a yellowish white oil, and removal of a small amount of hydrophilic components by centrifugation (2×10$^4$ G, 60 minutes, 20° C.) of this oil gave branched polyglycerol-modified silicone J-2 as a pale yellow oil (698 g).

Figure 6:
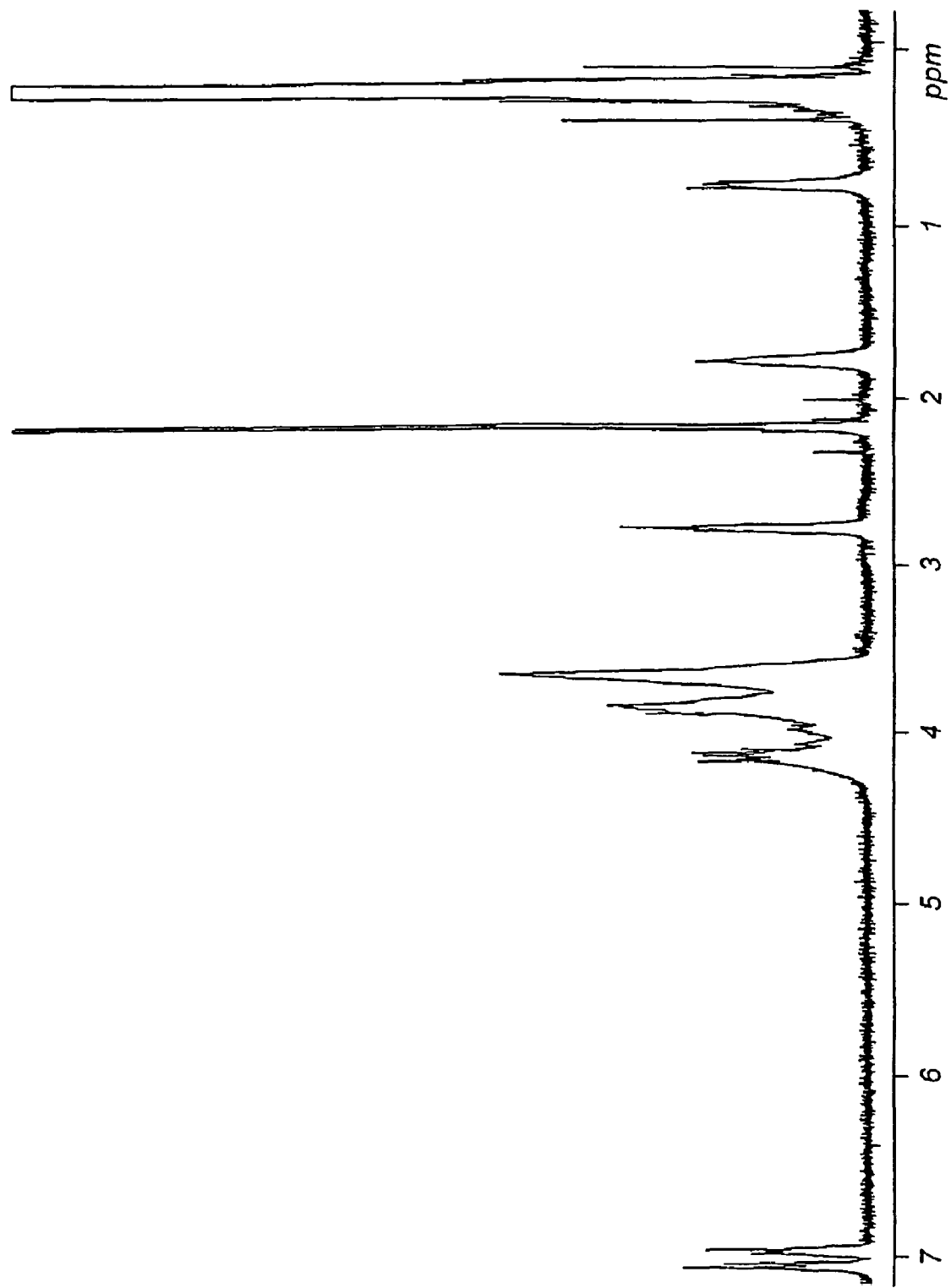
FIG. 6 is a $^1$H-NMR spectrum of the branched polyglycerol-modified silicone J obtained in Example 10.
Figure 7:
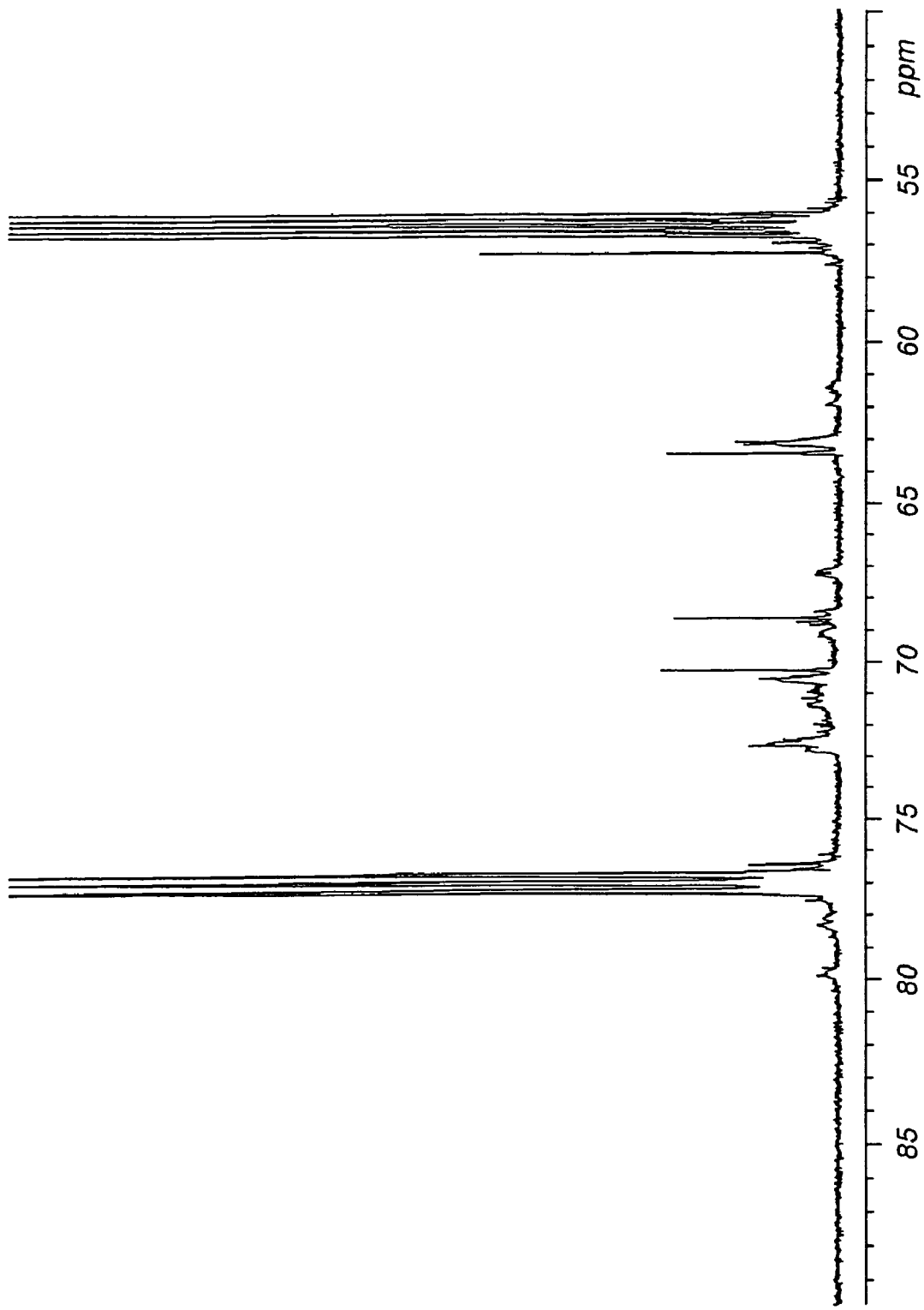
FIG. 7 is a $^{13}$C-NMR spectrum of the branched polyglycerol-modified silicone J obtained in Example 10.

$^1$H-NMR spectrum (acetone-$d_6$ solution) of branched polyglycerol-modified silicone J thus obtained is shown in FIG. 6, and $^{13}$C-NMR spectrum, in FIG. 7.

Example 11

Branched Polyglycerol-Modified Silicone K (Connecting Group: —CH$_2$CH$_2$CH$_2$—C$_6$H$_4$—O—)

Into a flask containing 913 g of phenol-modified silicone BY16-752 manufactured by Dow Corning Toray Silicone Co. Ltd., 42.7 g of 30% potassium methoxide methanol solution was added, and the mixture was heated to 60° C. under reduced pressure while being stirred to distill methanol off completely, to give a potassium salt of phenol-modified silicone as a yellow oil. To the modified silicone heated to 95° C., 236.7 g (5.3 equivalents) of glycidol was added by using a metering pump over a period of 5.7 hours while the mixture was stirred vigorously under an argon atmosphere. After heating and stirring additionally for 10 minutes, the mixture was allowed to cool to room temperature, to give a yellowish white paste product. Although the branched polyglycerol-modified silicone K obtained might be used as it was, it was stirred with 2,000 mL of ethanol, and the mixture was left standing, to separate into three phases. The transparent yellow supernatant, middle-phase highly viscous orange oil, and lower-phase turbid white oil were subjected to the cation-exchange treatment described in Example 9 and concentrated to give respectively a high-viscosity pale yellow oil material (637 g; branched polyglycerol-modified silicone K-1), a transparent pale yellow oil material (167 g; branched polyglycerol-modified silicone K-2), and a white paste (280 g; branched polyglycerol-modified silicone K-3). Total yield: 94.3%.

Figure 8:
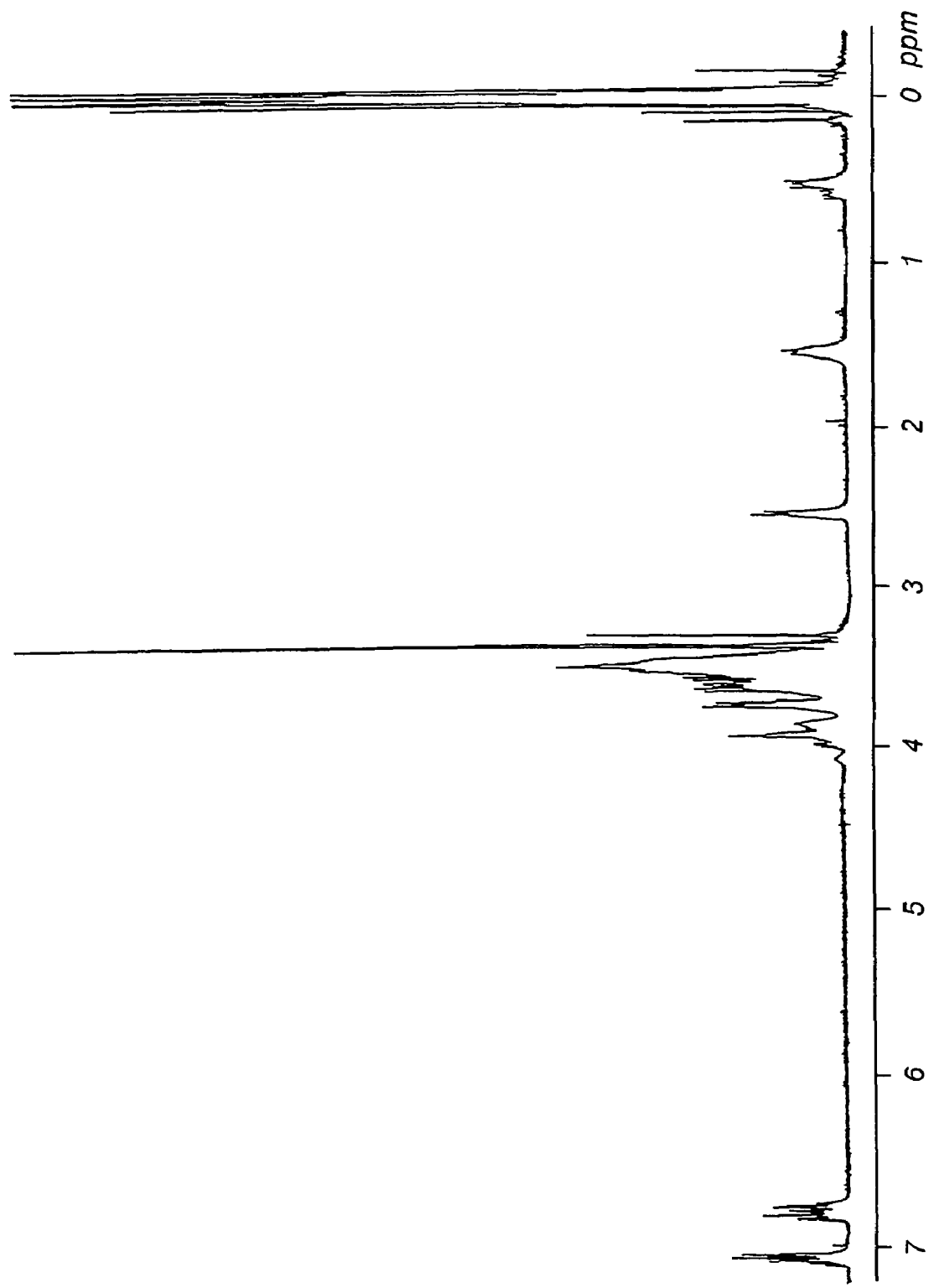
FIG. 8 is a $^1$H-NMR spectrum of the branched polyglycerol-modified silicone K obtained in Example 11.
Figure 9:
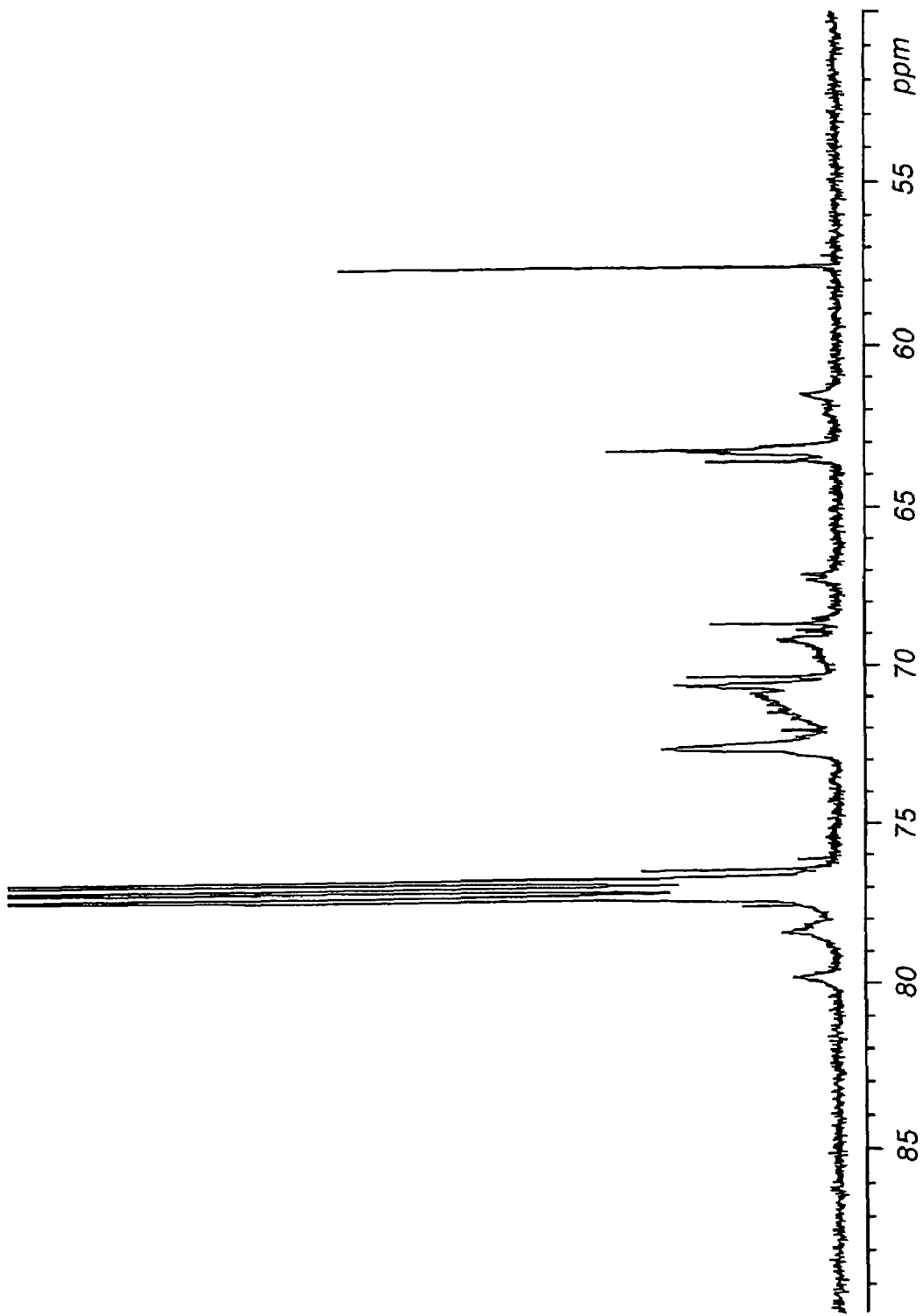
FIG. 9 is a $^{13}$C-NMR spectrum of the branched polyglycerol-modified silicone K obtained in Example 11.

$^1$H-NMR spectrum [chloroform-d/methanol-$d_4$ (4/1) solution] of branched polyglycerol-modified silicone K thus obtained is shown in FIG. 8, and $^{13}$C-NMR spectrum, in FIG. 9. Here, a=4.24, b=1.22, c=2.03, d=5.24, and a/(a+b+c+d)= 0.33.

Example 12

Branched Polyglycerol-Modified Silicone L (Connecting Group: —CH$_2$CH$_2$CH$_2$—C$_6$H$_4$—O—)

Figure 10:
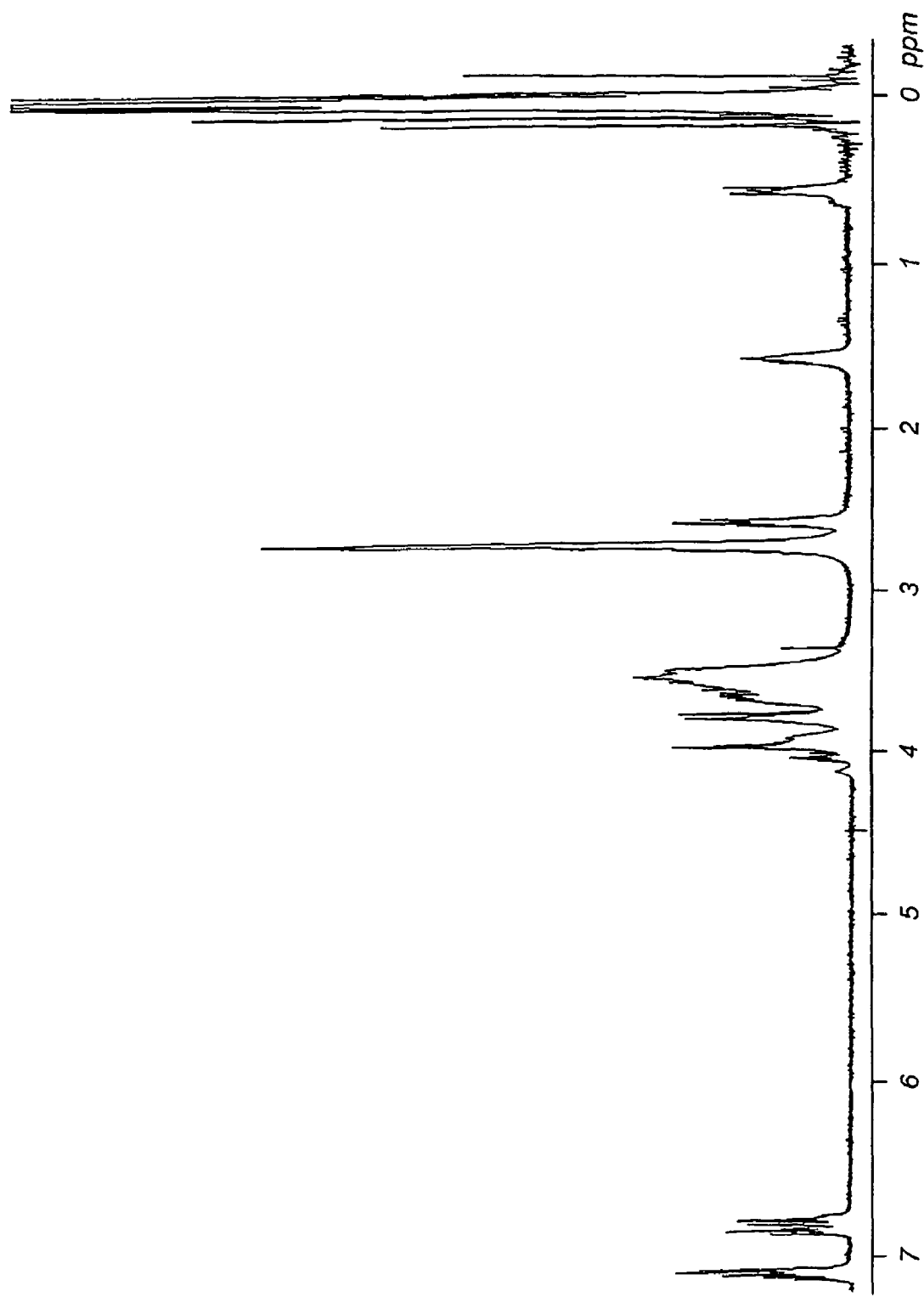
FIG. 10 is a $^1$H-NMR spectrum of the branched polyglycerol-modified silicone L-1 obtained in Example 12.
Figure 11:
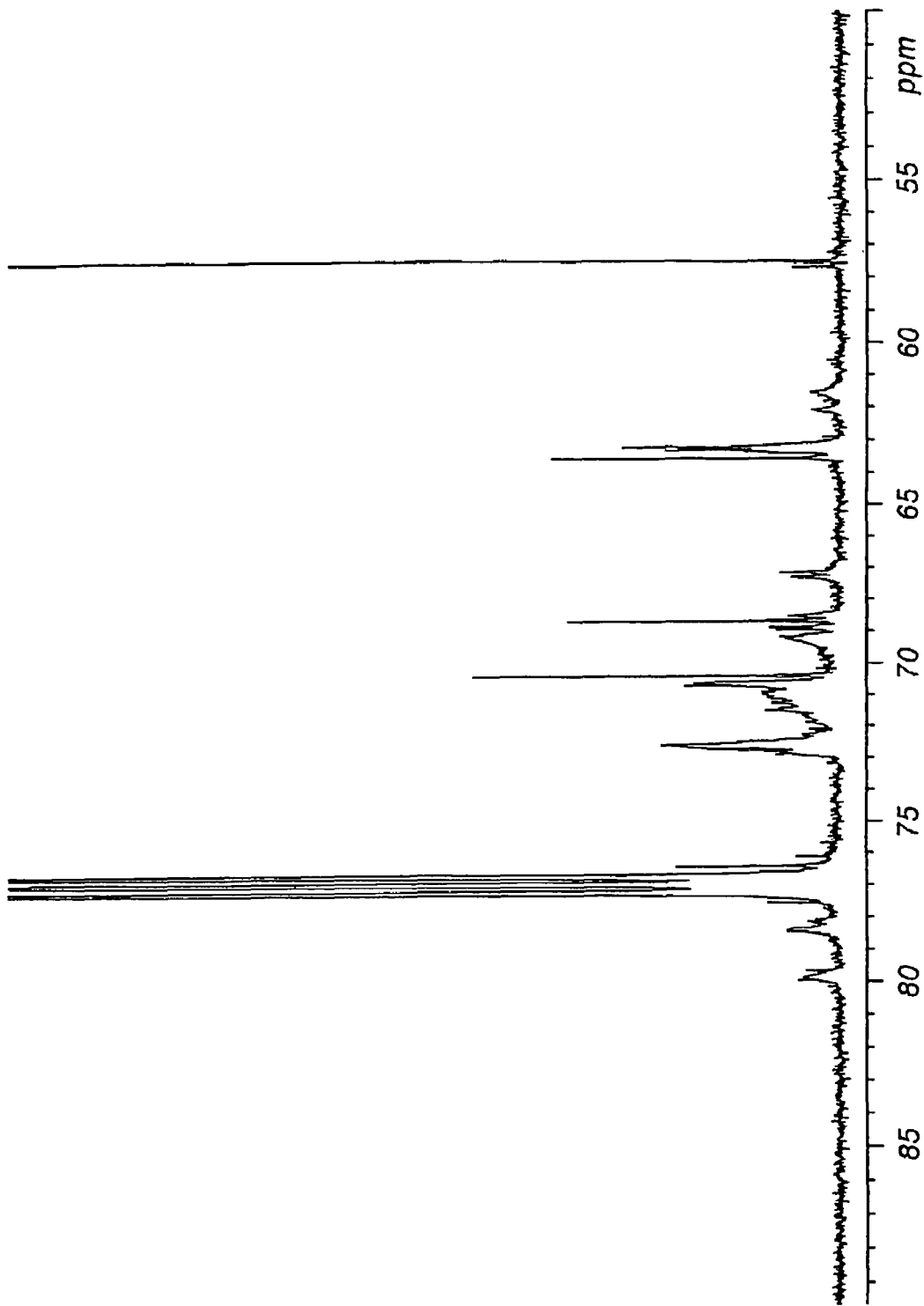
FIG. 11 is a $^{13}$C-NMR spectrum of the branched polyglycerol-modified silicone L-1 obtained in Example 12.
Figure 12:
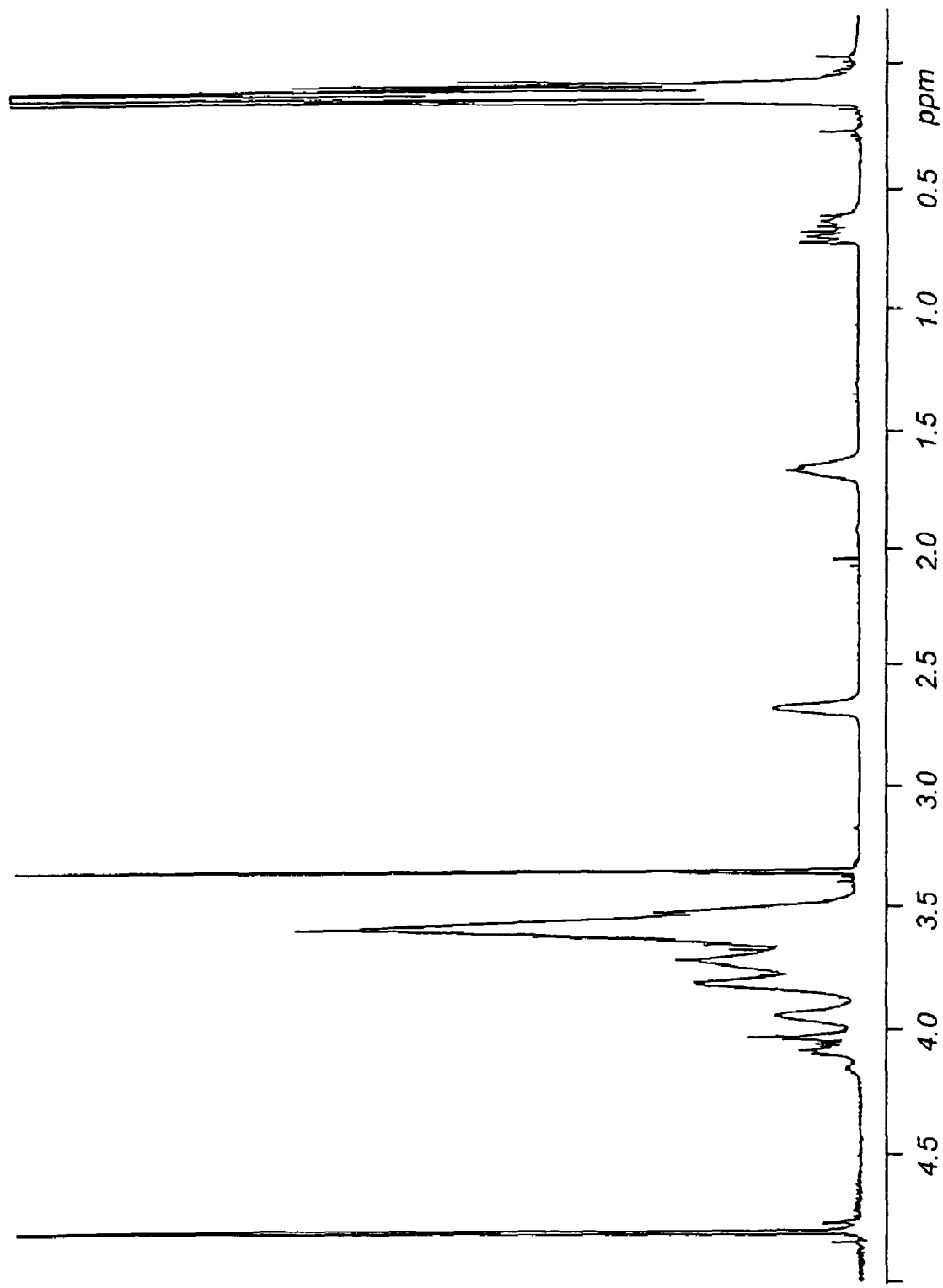
FIG. 12 is a $^1$H-NMR spectrum of the branched polyglycerol-modified silicone L-2 obtained in Example 12.
Figure 13:
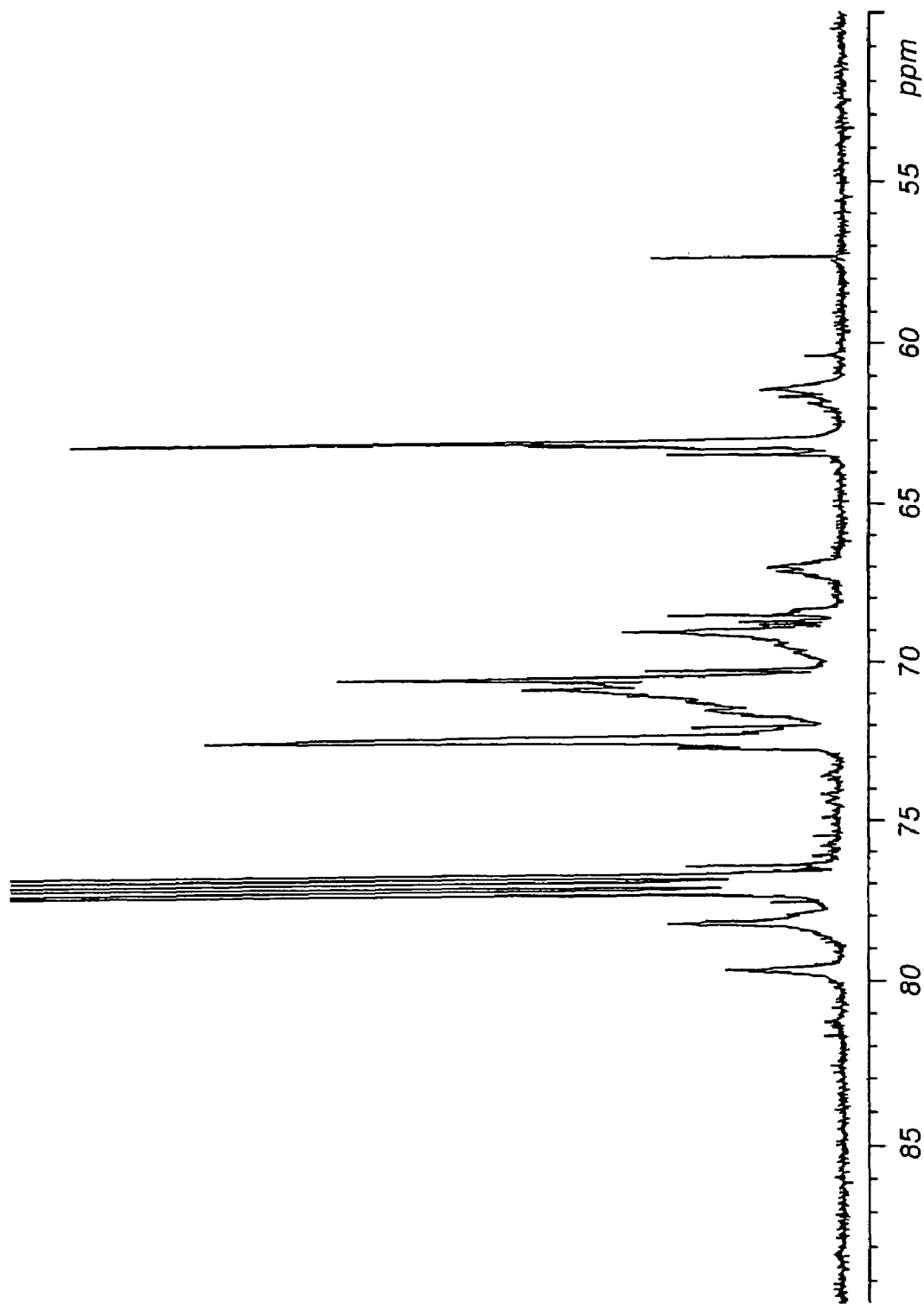
FIG. 13 is a $^{13}$C-NMR spectrum of the branched polyglycerol-modified silicone L-2 obtained in Example 12.

Polymerization similar to that described in Example 11 was carried out at 60° C., to give a yellowish white solid product. 1,000 mL of ethanol was added to the branched polyglycerol-modified silicone obtained, and the mixture was stirred and then allowed to stand and to be separated into two phases. The transparent pale yellow supernatant and the lower-phase orange oil were subjected to the cation-exchange treatment described in Example 9, to give respectively a pale yellow oil material (860 g; branched polyglycerol-modified silicone L-1) and an orange paste (275 g; branched polyglycerol-modified silicone L-2). Yield: 99.0%. $^1$H-NMR spectrum (chloroform-d/methanol-$d_4$ (9/1) solution) of branched polyglycerol-modified silicone obtained L-1 is shown in FIG. 10, and $^{13}$C-NMR spectrum, in FIG. 11. In addition, $^1$H-NMR spectrum (chloroform-d/methanol-$d_4$ (1/1) solution) of branched polyglycerol-modified silicone L-2 is shown in FIG. 12, and $^{13}$C-NMR spectrum, in FIG. 13.

Example 13

Branched Polyglycerol-Modified Silicone M (Connecting Group: —CH$_2$CH$_2$CH$_2$—C$_6$H$_4$—O—)

Into a flask containing 603 g of phenol-modified silicone BY16-799 manufactured by Dow Corning Toray Silicone [both ends modified, specific density: 0.99 g/ml, viscosity: 80 cSt, hydroxy group equivalence: 750 (average molecular weight: equivalent to 1,500), GPC (column: G4000HXL+ G2000HXL, THF solution (50 mmol/L acetic acid added), 40° C., as polystyrene), measured M$_n$=1,220, M$_w$=2,010], 16.9 g of 30% potassium methoxide methanol solution was added, and the mixture was heated to 60° C. under reduced pressure while being stirred to distill methanol off completely, to give a potassium salt of phenol-modified silicone as a yellow oil. To the modified silicone heated to 95° C., 119.1 g (2 equivalences) of glycidol was added by using a metering pump over a period of 5 hours while the mixture was stirred vigorously under an argon atmosphere. After heating and stirring additionally for 15 minutes, the mixture was allowed to cool to room temperature, to give a yellowish white wax product. Although branched polyglycerol-modified silicone K obtained might be used as it was, it was subjected to the desalination by cation-exchange treatment described in Example 9, and the resulting solution was concentrated, to give a branched polyglycerol-modified silicone M (713 g) as a high-viscosity yellow oil material. Yield: 96.7%.

Figure 14:
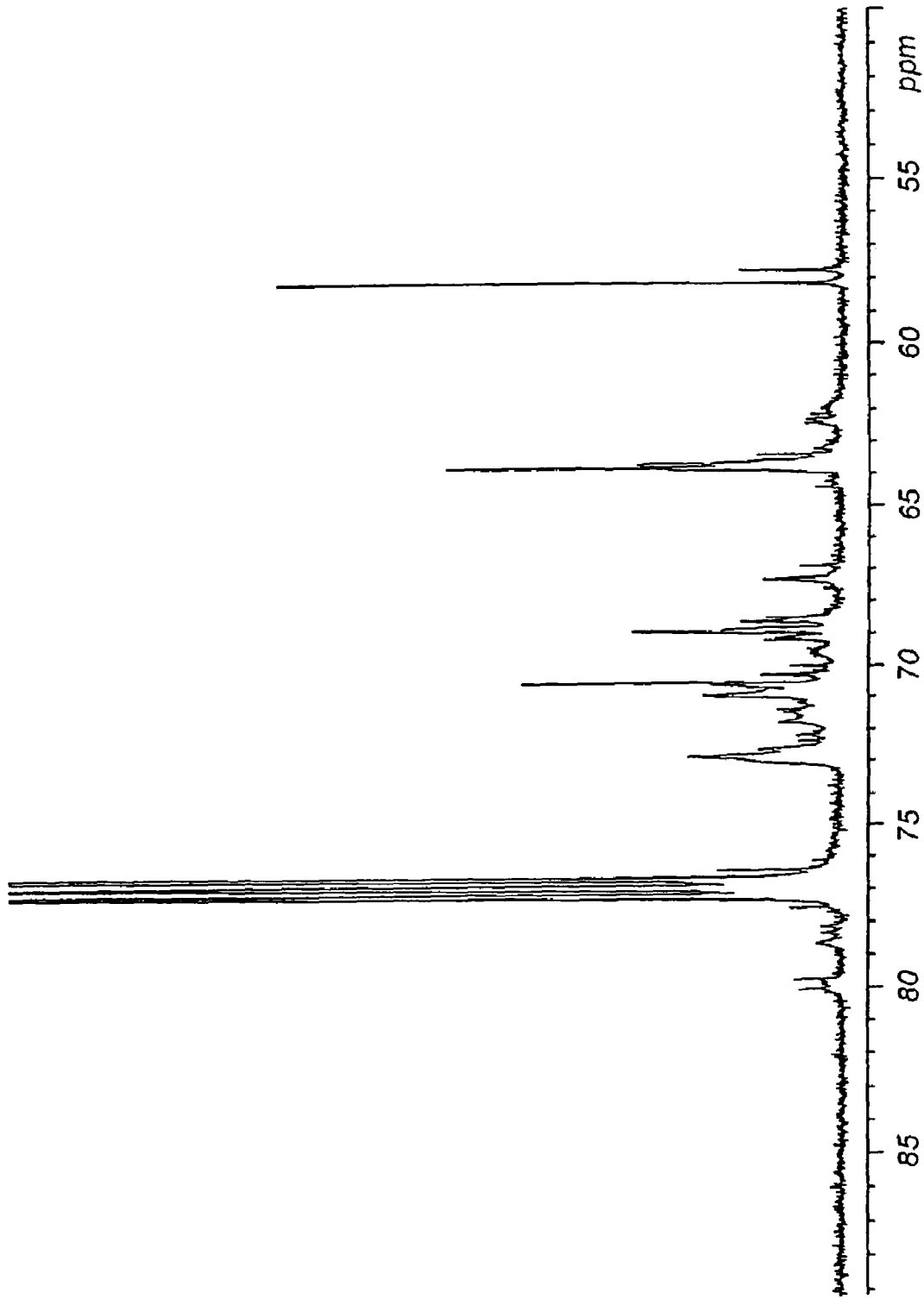
FIG. 14 is a $^{13}$C-NMR spectrum of the branched polyglycerol-modified silicone M obtained in Example 13.

$^{13}$C-NMR spectrum of branched polyglycerol-modified silicone M obtained is shown in FIG. 14.

Example 14

Branched Polyglycerol-Modified Silicone N (Connecting Group; —CH$_2$CH$_2$CH$_2$—C$_6$H$_4$—O—)

Into a flask containing 200 g of phenol-modified silicone X-22-1821 manufactured by Shin-Etsu Chemical Co. Ltd. [both ends modified, specific density: 0.99 g/mL, viscosity: 110 cSt, hydroxy group equivalence: 32 mg-KOH/g (average molecular weight: equivalent to 3,500)], 8.01 g of 30% potassium methoxide methanol solution was added, and the mixture was heated to 60° C. under reduced pressure while being stirred to distill methanol off completely, to give a potassium salt of phenol-modified silicone as a yellow oil. To the modified silicone heated to 95° C., 21.2 g (2.5 equivalences) of glycidol was added by using a metering pump over a period of 4 hours while the mixture was stirred vigorously under an argon atmosphere. After heating and stirring additionally for 15 minutes, the mixture was allowed to cool to room temperature, to give a transparent pale yellow paste product. Although the branched polyglycerol-modified silicone obtained might be used as it was, it was subjected to the desalination by cation-exchange treatment described in Example 9, and the resulting solution was concentrated to give branched polyglycerol-modified silicone N (213 g) as a highly viscous pale yellow oil material. Yield: 96.2%.

Example 15

Branched Polyglycerol-Modified Silicone O (Connecting Group; —CH$_2$CH$_2$CH$_2$—C$_6$H$_4$—O—)

Into a flask containing 150 g of phenol-modified silicone BY16-752 manufactured by Dow Corning Toray Silicone, 30 mL of 1 M potassium hydroxide ethanol solution was added, and the mixture was heated to 90° C. under reduced pressure while being stirred to distill water generated and ethanol off completely, to give a potassium salt of phenol-modified silicone as an orange red paste. To the modified silicone heated to 95° C., 230.6 g (4.1 equivalences) of glycidol was added by using a metering pump over a period of 3.7 hours while the mixture was stirred vigorously under an argon stream. After heating and stirring additionally for 10 minutes, the mixture was allowed to cool to room temperature, to give a yellowish white solid product. Although branched polyglycerol-modified silicone O obtained might be used as it was, it was stirred with 400 mL of ethanol, and the mixture was allowed to stand and be separated into two phases. The transparent yellow supernatant and the lower-phase highly viscous colorless oil were subjected to the desalination by cation-exchange treatment described in Example 9, to give respectively a yellow paste (143 g; branched polyglycerol-modified silicone O-1) and a turbid white oil material (29 g; branched polyglycerol-modified silicone O-2). Total yield: 95.2%.

Figure 15:
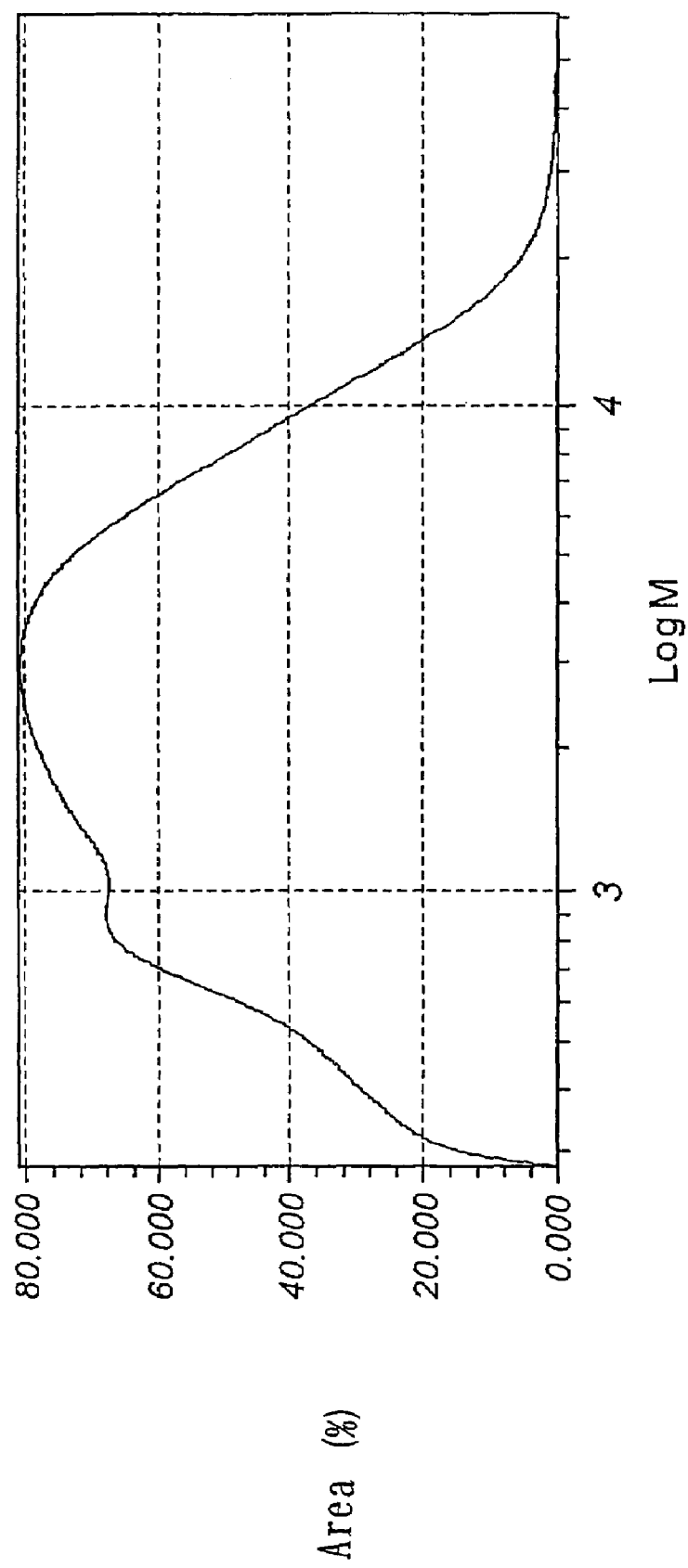
FIG. 15 is a chart illustrating the GPC results of branched polyglycerol-modified silicone O-1 obtained in Example 15.
Figure 16:
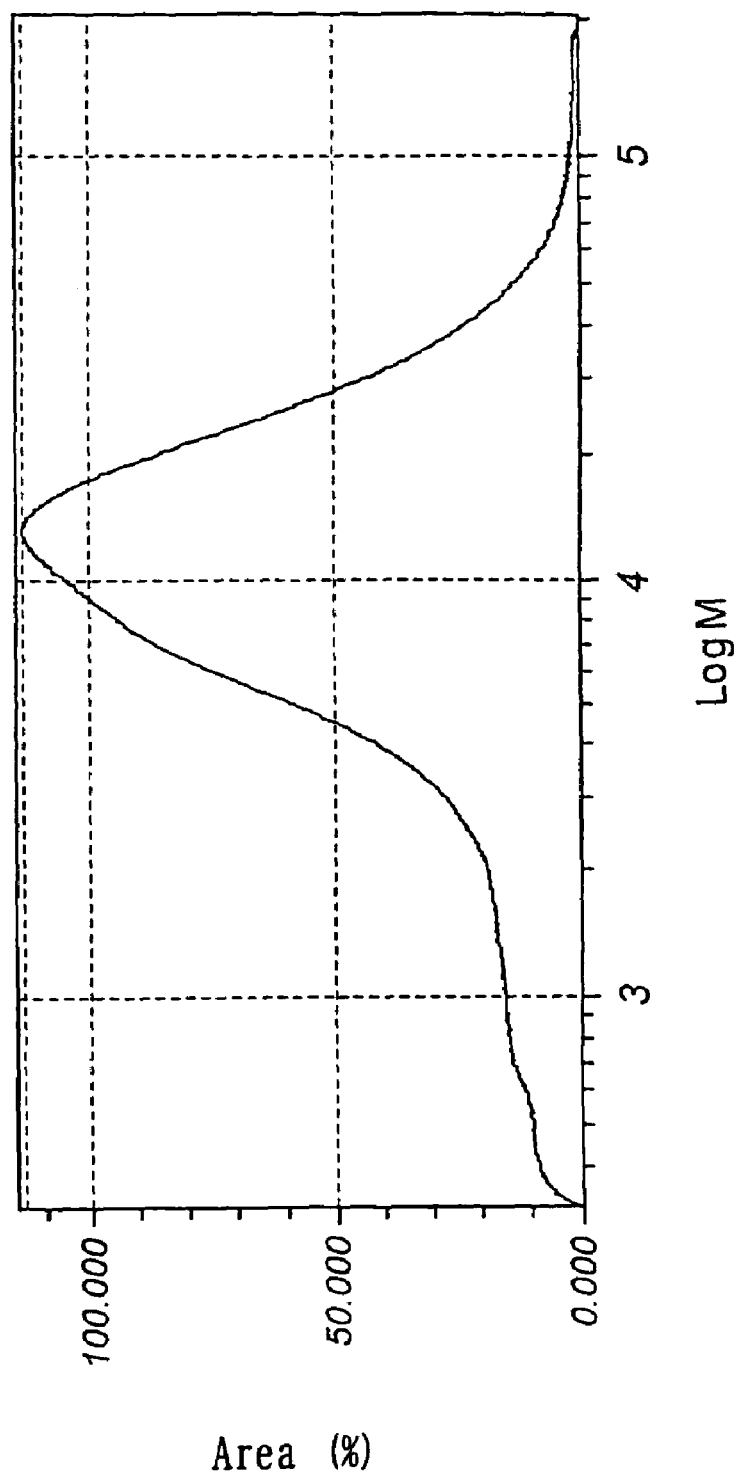
FIG. 16 is a chart illustrating the GPC results of branched polyglycerol-modified silicone O-2 obtained in Example 15.

Results of the GPC of branched polyglycerol-modified silicone obtained O-1 [column: G4000HXL+G2000HXL, THF solution (50 mmol/L acetic acid added), 40° C., as polystyrene] are shown in FIG. 15, and results of the GPC of branched polyglycerol-modified silicone O-2 [column: G4000HXL+G2000HXL, THF solution (50 mmol/L acetic acid added), 40° C., as polystyrene], in FIG. 16.

Example 16

Branched Polyglycerol-Modified Silicone P (Connecting Group; —CH$_2$CH$_2$CH$_2$—C$_6$H$_4$—O—)

Into a flask containing 500 g of phenol-modified silicone BY16-752 manufactured by Dow Corning Toray Silicone, 23.4 g of 30% potassium methoxide methanol solution was added, and the mixture was heated to 60° C. under reduced pressure while being stirred to distill methanol off completely, to give a potassium salt of phenol-modified silicone as a yellow oil. To the modified silicone heated to 95° C., 197.5 g (8 equivalences) of glycidol was added by using a metering pump over a period of 6.5 hours while the mixture was stirred under an argon atmosphere. After heating and stirring additionally for 20 minutes, the mixture was allowed to cool to room temperature, to give a pale yellowish white solid product. Although the obtained polyglycerol-modified silicone might be used as it was, it was stirred with 1,000 mL of ethanol/methanol mixture (4/1), and subjected to the desalination by the cation-exchange treatment described in Example 9. The resulting solution was concentrated, to give a branched polyglycerol-modified silicone P as a viscous pale yellowish white oil. Yield: 98%. Analysis of the $^{13}$C-NMR confirmed that modified silicone P was a branched polyglycerol-modified silicone having the group (1). Analysis of the $^1$H-NMR revealed that the modified silicon had a G of 17.3 (8.7 at each end), an Si of 38.5, and a G/Si ratio of 0.45.

To 300 g of branched polyglycerol-modified silicone P thus obtained, 100 mL of isopropyl alcohol was added. High-speed centrifugation (2×10$^4$ G, 60 minutes, 20° C.) separated the mixture into two phases. The upper phase was concentrated, to give an easily-soluble hydrophobic component as a white oil (209.1 g; branched polyglycerol-modified silicone P-1). On the other hand, concentration of the lower phase provided a hardly-soluble highly hydrophilic component as a highly viscous white paste (90.9 g; branched polyglycerol-modified silicone P-2).

Figure 17:
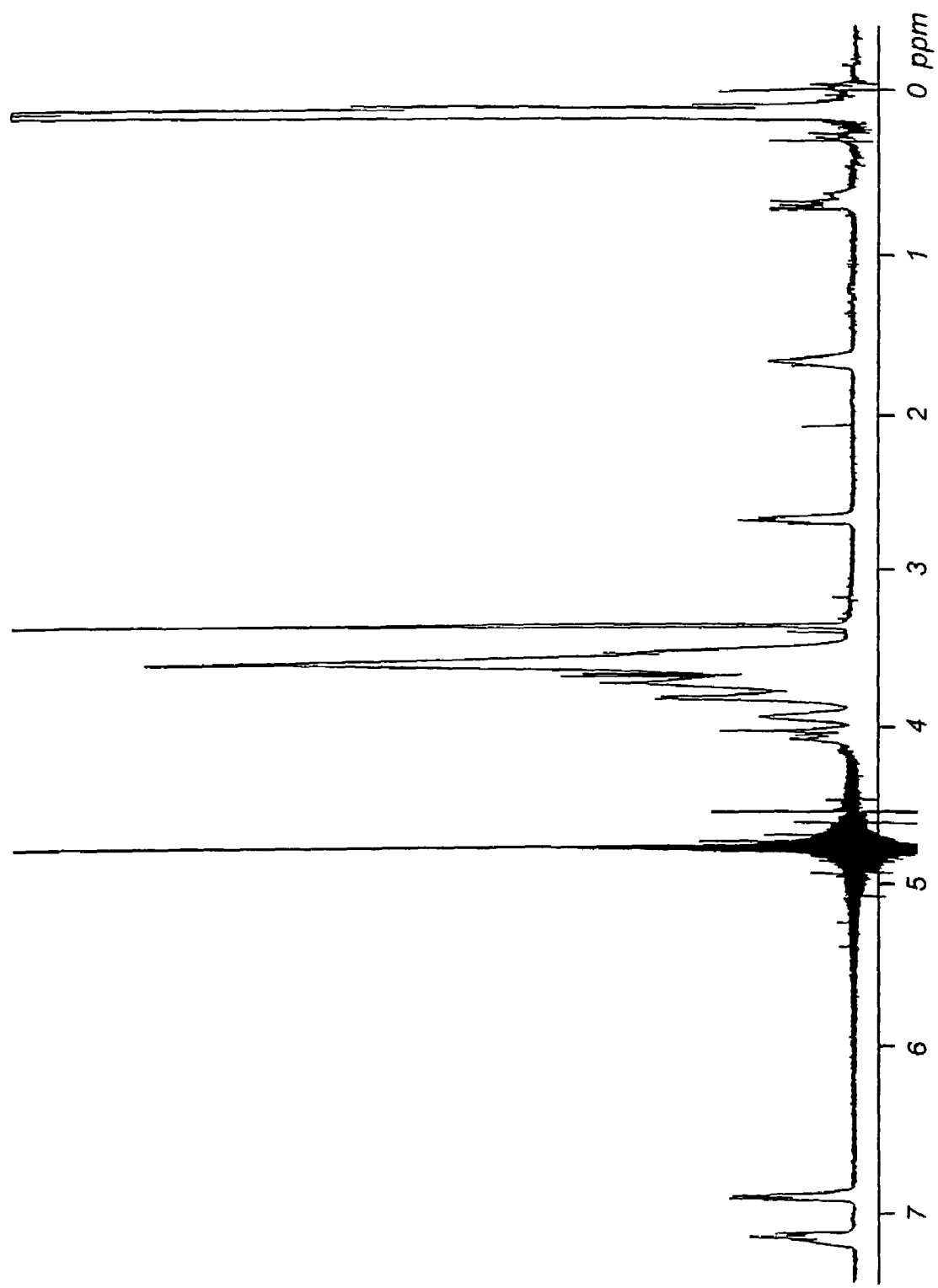
FIG. 17 is a $^1$H-NMR spectrum of the branched polyglycerol-modified silicone P obtained in Example 16.
Figure 18:
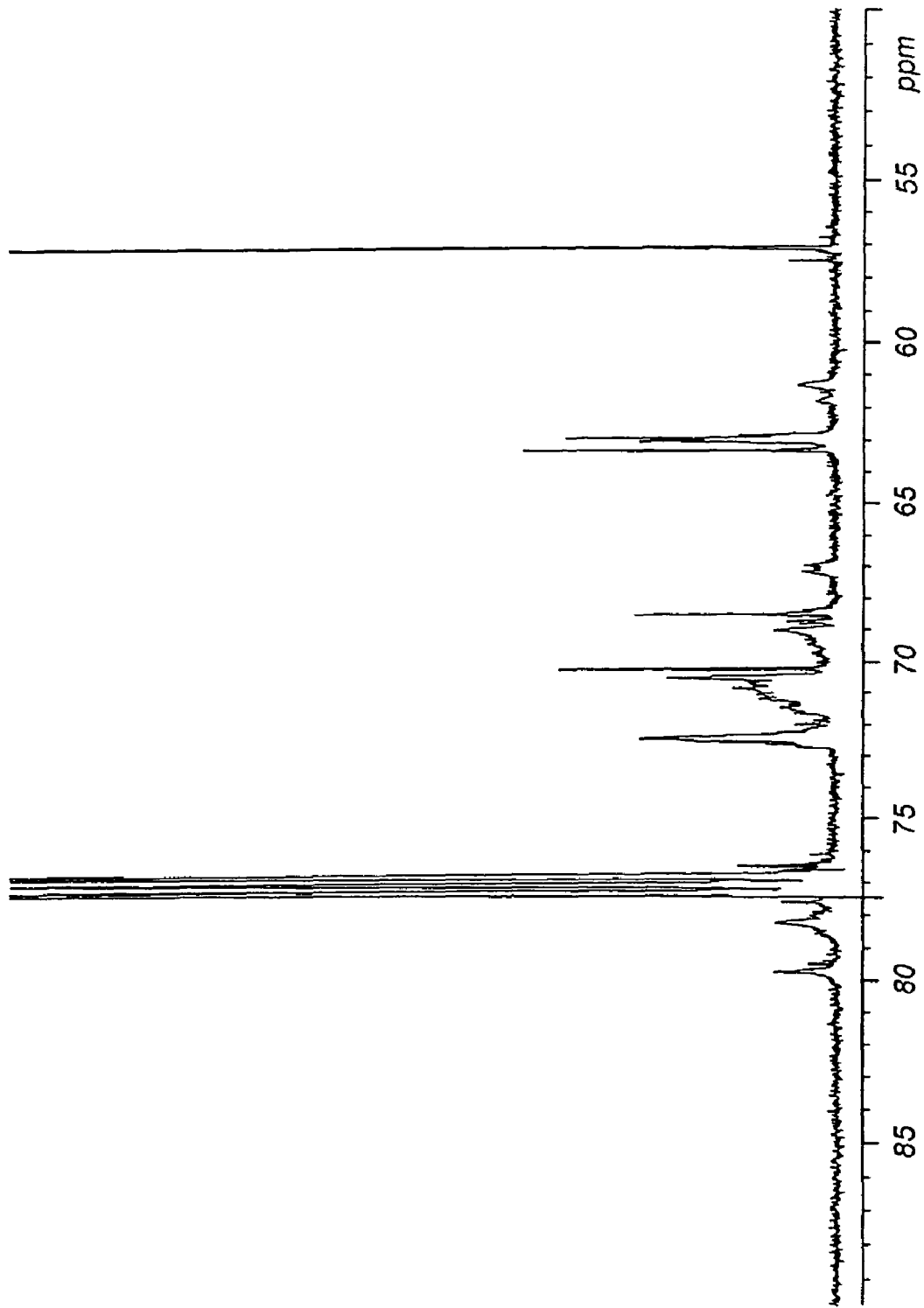
FIG. 18 is a $^{13}$C-NMR spectrum of the branched polyglycerol-modified silicone P-1 obtained in Example 16.
Figure 19:
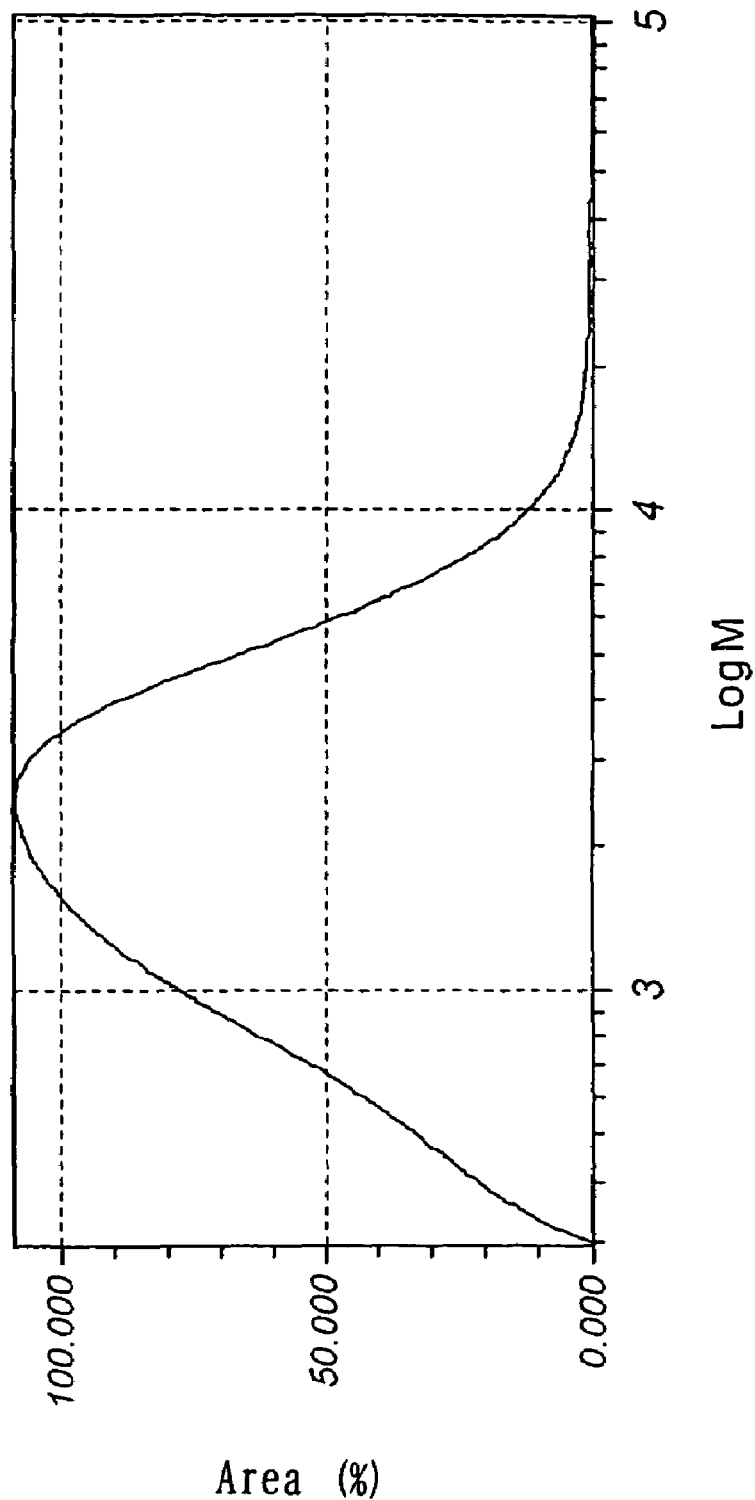
FIG. 19 is a chart illustrating the GPC results of branched polyglycerol-modified silicone P-2 obtained in Example 16.

$^1$H-NMR spectrum of branched polyglycerol-modified silicone P thus obtained [methanol-$d_4$/chloroform-d (4/1) solution] is shown in FIG. 17; $^{13}$C-NMR spectrum of branched polyglycerol-modified silicone P-1, in FIG. 18; results of the GPC of branched polyglycerol-modified silicone P-2 [column: α-M (manufactured by Tosoh Corporation)×2, DMF solution (50 mmol/L LiBr added), 40° C., as polyethylene oxide], in FIG. 19.

Example 17

Branched Polyglycerol-Modified Silicone Q (Connecting Group: —CH$_2$CH$_2$CH$_2$—C$_6$H$_4$—O—)

Into a flask containing 200 g of phenol-modified silicone X-22-1897 manufactured by Shin-Etsu Chemical Co. Ltd. [both ends modified, specific density: 0.98 g/mL, viscosity: 317 cSt, hydroxy group equivalence: 11.5 mg-KOH/g (average molecular weight: equivalent to 9,760), GPC (column: G4000HXL+G2000HXL, THF solution (50 mmol/L acetic acid added), 2.9 g of 30% potassium methoxide methanol solution was added, and the mixture was heated to 60° C. under reduced pressure while being stirred to distill methanol off completely, to give a potassium salt of phenol-modified silicone as a pale yellowish brown oil. To the modified silicone heated to 95° C., 30.4 g (10 equivalences) of glycidol was added by using a metering pump over a period of 5 hours while the mixture was stirred vigorously under an argon atmosphere. After heating and stirring additionally for 15 minutes, the mixture was allowed to cool to room temperature, to give a highly viscous semi-transparent paste product. Although the branched polyglycerol-modified silicone obtained might be used as it was, it was subjected to the desalination by cation-exchange treatment described in Example 9, and the resulting solution was concentrated to give branched polyglycerol-modified silicone Q (226 g) as a highly viscous white oil material. Yield: 98.1%. As branched polyglycerol-modified silicone Q is not soluble uniformly in the GPC-measuring solvent, 100 g of the oil was centrifuged (2×10$^4$ G, 60 minutes, 20° C.) to separate into two phases. The upper phase was a milky white oil material (91.9 g, branched polyglycerol Q-1), and the lower phase, a pale orange paste material (8.1 g, branched polyglycerol Q-2).

Figure 20:
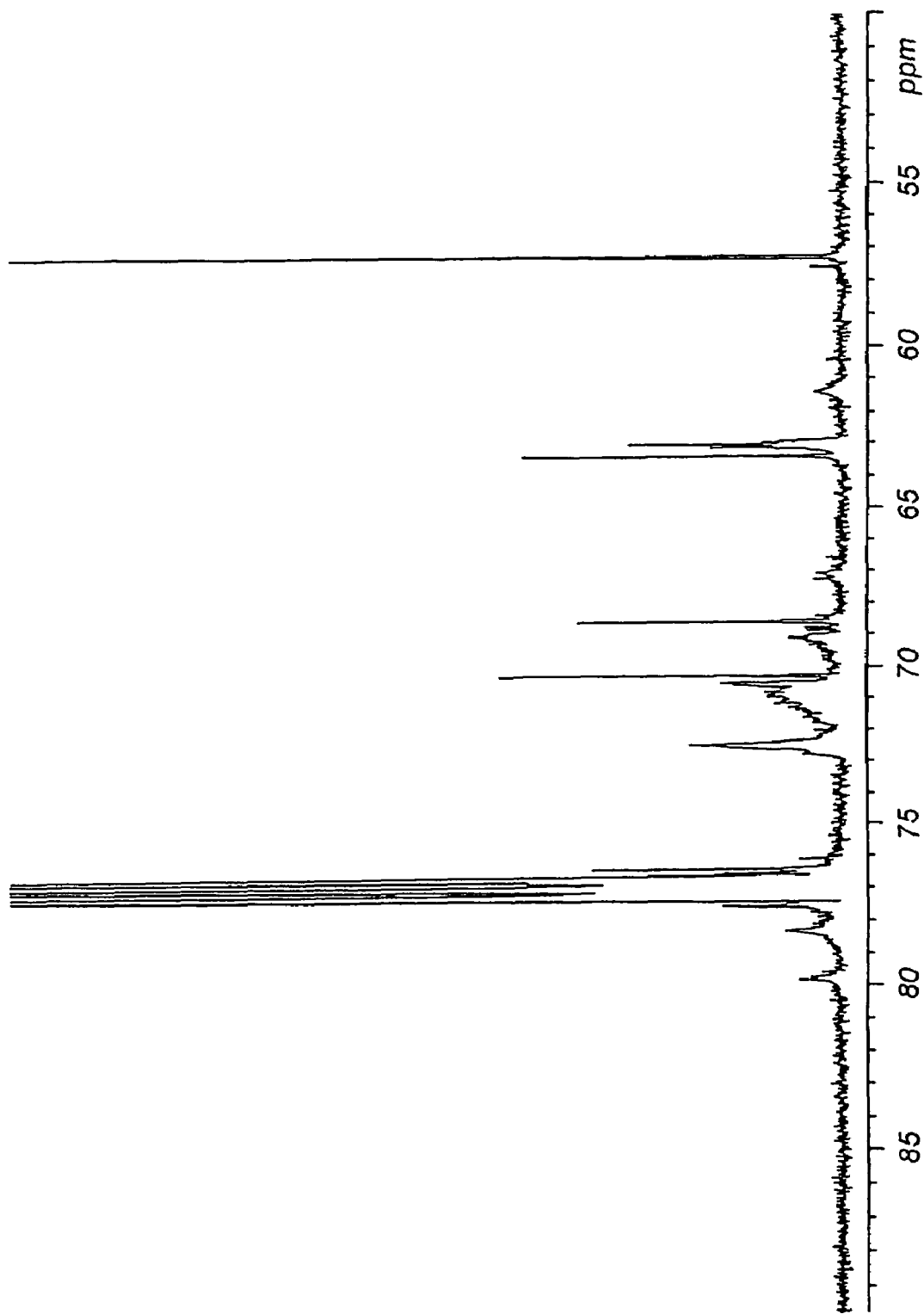
FIG. 20 is a $^{13}$C-NMR spectrum of the branched polyglycerol-modified silicone Q-1 obtained in Example 17.

$^{13}$C-NMR spectrum of branched polyglycerol-modified silicone Q-1 obtained is shown in FIG. 20.

The compositions and molecular weights of various branched polyglycerol-modified silicones obtained in Examples 9 to 17 are summarized in Table 1.

TABLE 1

| Example No. | Branched polyglycerol-modified silicone | Composition | | | Molecular weight* | |
| --- | --- | --- | --- | --- | --- | --- |
| | | G | Si | rate of G/Si | Mn | Mw |
| 9 | I | 8.6 | 31.9 | 0.27 | 2650 | 5820 |
| 10 | J-1 | 6.9 | 29.7 | 0.23 | 1030 | 2690 |
| | J-2 | 7.6 | 45.8 | 0.16 | 1820 | 5820 |
| 11 | K-1 | 10.9 | 27.4 | 0.40 | 1410 | 3580 |
| | K-2 | 12.1 | 20.2 | 0.60 | 990 | 1740 |
| | K-3 | 3.4 | 40.9 | 0.008 | 5950 | 9350 |
| 12 | L-1 | 7.2 | 52.4 | 0.18 | 2560 | 6450 |
| | L-2 | 16.4 | 12.2 | 1.34 | 880 | 1800 |
| 13 | M | 4.0 | 13.0 | 0.31 | 1280 | 7900 |
| 14 | N | 5.2 | 38.5 | 0.14 | 1690 | 4830 |
| 15 | O-1 | 10.0 | 26.9 | 0.37 | 1440 | 3560 |
| | O-2 | 6.2 | 230.2 | 0.027 | 4360 | 1317 |

TABLE 1-continued

| Example No. | Branched polyglycerol-modified silicone | Composition | | | Molecular weight* | |
| --- | --- | --- | --- | --- | --- | --- |
| | | G | Si | rate of G/Si | Mn | Mw |
| 16 | P-1 | 8.7 | 66.2 | 0.13 | 2040 | 6990 |
| | P-2 | 28.8 | 7.0 | 4.11 | 1480 | 2710 |
| 17 | Q | 20.4 | 125.7 | 0.16 | — | — |
| | Q-1 | 8.5 | 125.3 | 0.068 | 8160 | 18190 |
| | Q-2 | — | — | — | 1480 | 2680 |

*$M_n$ represents the number-average molecular weight; and $M_w$, the weight-average molecular weight. The conditions for analyzing the molecular weight by GPC are as follows:

For P-2 and Q-2, column: α-M (manufactured by Tosoh Corporation)×2, eluant: DMF (50 mmol/L LiBr added), 40° C., as polyethylene oxide; and for others, column: G4000HXL+G2000HXL (manufactured by Tosoh Corporation), eluant: THF (50 mmol/L acetic acid added), 40° C., as polystyrene.

Comparative Example 1

Straight-chain polyglycerol-modified silicone An allyl polyglycerol ether was prepared according to the method described in Example 1 of Japanese Patent Publication B No. 62-34039. This ether and 1,1,1,3,5,7,7,7-octamethyltetrasiloxane (LS-8630, manufactured by Shin-Etsu Chemical Co. Ltd.) were reacted according to the method described in Example 8 of the same patent publication, to give a straight-chain polyglycerol-modified silicone compound (hereinafter, referred to as comparative silicone 1).

Test Example 1

The residual amounts of silicones on fabrics were evaluated according to the method described below, by using branched polyglycerol-modified silicones A to D obtained in Examples 1 to 4, comparative silicone 1, and comparative silicones 2 to 4 described below. Results are summarized in Table 2.

<Comparative Silicones>

Comparative silicone 2: polyether-modified silicone at both ends, manufactured by Dow Corning Toray Silicone Co. Ltd. SF8427; OH equivalence: 1,200 (average molecular weight: equivalent to 2,400). Comparative silicone 3: Side-chain amino-modified silicone, TSF4702, manufacture by GE Toshiba Silicones; OH equivalence: 1,600; viscosity: 500 mPa·s. Comparative silicone 4: Dimethylsilicone, TSF451-1000, manufacture by GE Toshiba Silicones; viscosity: 1,000 mPa·s.

<Method of Evaluating the Residual Adsorption Amount of Silicone on Fabrics>

A solution of 0.0133 g of each of the silicone compounds and 6 L of water (containing only silicone); a solution of 0.0133 g of each of the silicone compounds, 0.0013 g of a nonionic surfactant (polyoxyethylene laurylether), and a 6 L of water (containing the nonionic surfactant at 10%); and a solution of 0.0133 g of each of the silicone compounds, 0.0267 g of a cationic surfactant (dimethyldistearylammonium chloride), and 6 L of water (containing the cationic surfactant at 200%) were preliminary stirred for 1 minute. 200 g of cotton pile fabric (previously washed and rinsed thoroughly and dried) was immersed and stirred in each of these solutions for 5 minutes, and removed, centrifuged by a washing machine, and air-dried in an air-conditioned room at 20° C. and a relative humidity of 35% for 24 hours. The amount of silicon atom remaining on each of the test fabrics thus processed was determined by ICP analysis. The amount of silicon contained inherently in the fabric was estimated from the analytical values of the cotton fabrics processed only with water. Separately, the amount of silicon present on the cotton fabrics whereon the same amount of the silicone compound was directly applied was determined quantitatively, from which the residual adsorptivity of each of the silicone compounds was calculated.

TABLE 2

| | | Residual absorption rate of silicone on fabric (%) | | |
|---|---|---|---|---|
| | Silicone | Only silicone | Nonionic surfactant added at 10% | Cationic surfactant added at 200% |
| Product of the invention | Branched polyglycerol-modified silicone A | 38 | 65 | 88 |
| | Branched polyglycerol-modified silicone B | 27 | 39 | 52 |
| | Branched polyglycerol-modified silicone C | 42 | 51 | 72 |
| | Branched polyglycerol-modified silicone D | 31 | 48 | 61 |
| Compatrative product | Comparative silicone 1 | 7 | 9 | 15 |
| | Comparative silicone 2 | 5 | 8 | 11 |
| | Comparative silicone 3 | 13 | 18 | 21 |
| | Comparative silicone 4 | <3 | 5 | 8 |

Test Example 2

The branched polyglycerol-modified silicone A obtained in Example 1 and the comparative silicones 1 and 2 for comparison were respectively blended in a commercially available body shampoo "Weakly Acidic Biore, Mild Floral Flavor" at the content of 0.5% by weight, and the solutions were subjected to the following skin-cleansing test. Results are shown in Table 3.

<Skin-Cleansing Test>

Three test items, foaming, foam quality, and skin wetness after rinse, of the body shampoos containing respective silicone compounds are compared with those of the body shampoo without the compounds, and the results were digitalized according to the points shown below. The full marks are +6.

+2: Significantly superior to the commercial product

+1: Superior to commercial product

0: Similar to commercial product

−1: Inferior to commercial product

−2: Significantly inferior to commercial product

TABLE 3

| | | Sensory index (full marks of +6) | | |
|---|---|---|---|---|
| | Silicone blended | lather | lather quantity | Skin wetness |
| Product of the invention | Branched polyglycerol-modified silicone A | +4 | +6 | +6 |
| Comparative product | Comparative silicone 1 | +2 | +2 | 0 |
| | Comparative silicone 2 | −6 | −5 | −1 |

As apparent from Table 3, the volume and quality of lather of the body shampoo containing the inventive product were improved drastically, providing very preferable wet and skin-protecting feeling after rinse.

Test Example 3

The interfacial tensions of branched polyglycerol-modified silicone, I, J-1, K, L-1, M, N, O, P, and P-1, obtained in Examples, the comparative silicones 1 and 2, and the following comparative silicone 5 at methylcyclohexane/water and dimethyl silicone/water interfaces were determined according to the following method. Results are summarized in Table 4.

<Comparative Silicone>

Comparative silicone 5: Commercial available silicone phenol-modified at both ends, X-22-1821, manufactured by Shin-Etsu Chemical Co. Ltd.

<Method of Determining Interfacial Tension>

The interfacial tension was determined according to the spinning drop method [A.C.S. Symp. Ser., 8, "Adsorption at Interfaces", p. 234 (1975)]. A drop of oil containing a silicone compound at 0.2% [methylcyclohexane or dimethylsilicone (viscosity: 10 cSt)] was injected into deionized and distilled water placed in a glass tube (internal diameter: 3.00 mm, external diameter: 6.00 mm, length: 95.50 mm) having a refractive index of 1.332, and the glass tube is rotated at high speed. After the system comes reached the equilibrium (after 30 minutes or more), the interfacial tension is determined from the measured degree of deformation of the oil droplet. Temperature; 25.0° C., rotational velocity: 8888.9 r/min.

TABLE 4

| | | Interfacial tension (dyne/cm) | |
|---|---|---|---|
| | Silicone | methylcyclohexane/water | Dimethyl silicone/water |
| Product of the invention | Branched polyglycerol-modified silicone I | 12.11 | 3.95 |
| | Branched polyglycerol-modified silicone J-1 | 2.79 | 0.328 |
| | Branched polyglycerol-modified silicone K | 6.42 | 1.93 |
| | Branched polyglycerol-modified silicone L-1 | 9.99 | 3.50 |

TABLE 4-continued

|  | Silicone | Interfacial tension (dyne/cm) | |
|---|---|---|---|
|  |  | methylcyclohexane/water | Dimethyl silicone/water |
|  | Branched polyglycerol-modified silicone M | 0.813 | 0.808 |
|  | Branched polyglycerol-modified silicone N | 4.72 | 2.13 |
|  | Branched polyglycerol-modified silicone O | 2.18 | 0.92 |
|  | Branched polyglycerol-modified silicone P | 8.62 | 4.06 |
|  | Branched polyglycerol-modified silicone P-1 | 10.82 | 8.16 |
| Comparative product | Comparative silicone 1 | 16.54 | 9.10 |
|  | Comparative silicone 2 | 8.11 | 5.17 |
|  | Comparative silicone 5 | 16.81 | 10.18 |

As apparent from Table 4, branched polyglycerol-modified silicones J-1, M, and O have a notably higher surface activity than conventional modified silicones.

Test Example 4

Cotton fabrics were treated with each of branched polyglycerol-modified silicones, J, K, L-1, M, and Q-1, obtained Examples and the comparative silicones 1 to 4 for comparison according to the method described below, and the residual adsorptivity and the feeling (feeling to the touch) of the fabrics treated with each of the silicone compounds were evaluated. Results are summarized in Table 5.

<Evaluation Methods>

(1) Treatment of Cotton Fabrics with Various Silicone Compounds 0.13 g of each of the silicone compounds (containing only silicone); 0.133 g of each of the silicone compounds and 0.0133 g of a nonionic surfactant (polyoxyethylene laurylether) (containing nonionic surfactant at 10%); or 0.133 g of each of the silicone compounds and 0.267 g cationic surfactant (dimethyldistearylammonium chloride) (containing a cationic surfactant at 200%) was added into a washing machine filled with 60 L of water and stirred preliminary for 3 minutes. Twenty seven pieces of cotton pile fabrics (32×75 cm, about 75 g; previously washed and rinsed thoroughly and dried) were immersed therein and stirred for 5 minutes, centrifuged (3 minutes), and removed therefrom, and dried in an air-conditioned room at 20° C. and a relative humidity of 35% for 24 hours. For comparison, cotton cloths (standard cotton cloths) respectively treated only with water, 0.0133 g of the nonionic surfactant, and 0.267 g of the cationic surfactant were prepared in a similar manner.

(2) Determination of the Residual Adsorptivity on Fabrics

The amount of residual silicone compound adsorbed on each treated cloth was determined by elementary analysis of silicon by using an ICP method. The amount of silicon inherently contained in the cotton cloth was determined from the measured value of the cotton cloth treated only with water, and the measured values above were subtracted with this value. Separately, the amount of silicon contained in the cotton cloth treated directly with the same amount of silicone compound was determined, and the residual adsorptivity of each of the silicone compounds after the water-washing treatment was calculated.

(3) Method of Sensory Evaluation

The feeling (feeling to the touch) of the silicone-treated cotton cloth was compared to that of the corresponding standard cotton cloth (only treated with water, with a nonionic surfactant, or with a cationic surfactant) in a manner similar to the method above. Three cotton cloths were respectively subjected to sensory evaluation by ten evaluation panelists. The results of sensory evaluation were digitalized according to the following points, and evaluated based on total points (full marks of +60).

+2: Very preferable compared to standard cotton cloth

+1: Preferable compared to standard cotton cloth

0: Similar to the standard cotton cloth

−1: Unpreferable compared to standard cotton cloth

−2: Very unpreferable compared to standard cotton cloth

TABLE 5

|  |  | Fabric residual absorption rate (%) | | | Sensory index (full marks of +60) | | |
|---|---|---|---|---|---|---|---|
|  | Silicone | Only silicone | Nonionic surfactant added at 10% | Cationic surfactant added at 200% | Only silicone | Nonionic surfactant added at 10% | Cationic surfactant added at 200% |
| Product of the invention | Branched polyglycerol-modified silicone J | 45 | 63 | 94 | +48 | +59 | +60 |
|  | Branched polyglycerol-modified silicone K | 42 | 64 | 98 | +59 | +60 | +60 |
|  | Branched polyglycerol-modified silicone L-1 | 38 | 52 | 86 | +41 | +56 | +57 |
|  | Branched polyglycerol-modified silicone M | 39 | 47 | 72 | +44 | +55 | +55 |
|  | Branched polyglycerol-modified silicone Q-1 | 41 | 58 | 96 | +45 | +58 | +60 |
| Comparative product | Comparative silicone 1 | 7 | 9 | 15 | +1 | −12 | +14 |
|  | Comparative silicone 2 | 5 | 8 | 11 | −42 | −54 | −59 |

TABLE 5-continued

| | Fabric residual absorption rate (%) | | | Sensory index (full marks of +60) | | |
|---|---|---|---|---|---|---|
| Silicone | Only silicone | Nonionic surfactant added at 10% | Cationic surfactant added at 200% | Only silicone | Nonionic surfactant added at 10% | Cationic surfactant added at 200% |
| Comparative silicone 3 | 13 | 18 | 21 | +18 | +11 | +23 |
| Comparative silicone 4 | <3 | 5 | 8 | +7 | +3 | +1 |

As apparent from Table 5, the branched polyglycerol-modified silicones according to the invention remain adsorbed on fabrics at an extent drastically higher than conventional modified silicone compounds, even when the fabrics are treated in a very dilute concentration. The extent of adsorption thereof is much higher than that of the comparative silicone 3 (amino-modified silicone), which is commonly said to have a high adsorptivity to fabrics, hair, and skin. Although not wanting to be limited by theory, because the comparative silicone 1, a straight-chain polyglycerol-modified silicone having a similar composition, does not have such a high residual adsorption property, the high adsorptivity of the branched polyglycerol-modified silicones according to the invention onto fabrics seems to be derived from the polyglycerol groups having developed branched structures and thus inherent thereto.

In addition, the branched polyglycerol-modified silicones according to the invention are extremely superior in fabric-processing capacity, and provide fabrics with very preferable feeling to the touch even when used in a smaller amount. One of the factors for the commercially extremely valuable property is likely the very high residual adsorptivity of the inventive silicones described above. At the same time, although not wanting to be limited by theory, from the fact that comparative silicone 2 (polyether-modified silicone), which has been used widely in various areas as a highly hydrophilic modified silicone, deteriorates the feeling of treated cloths as the residual adsorptivity increases (silicone-only system<nonionic surfactant system<cationic surfactant system) and such preferable feeling cannot be obtained on the cloths treated with the straight-chain polyglycerol-modified silicone (comparative silicone 1) having a similar structure, it is reasonable to consider that the phenomenon that the inventive branched polyglycerol group is strongly adsorbed by orienting many highly adsorptive terminal hydroxy groups on the fabric surface (because of its higher content of primary hydroxy groups) and thus the flexible silicone main chains are efficiently oriented on the utmost external surface of the fabrics is one of the major factor for the preferable fabric-processing efficiency.

The invention claimed is:

1. A branched polyglycerol-modified silicone, comprising at least one branched polyglycerol chain comprising at least one branched glycerol group represented by the below shown formula (1) and being connected via a connecting group to a silicon atom of the silicone

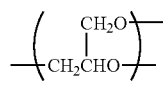
(1)

wherein said group of formula (1) which is connected to said silicon atom via said connecting group is bonded to said connecting group via the available —CH$_2$ group and the two oxygen atoms in said group of formula (1), independently of each other, bind to a glycerol or glycidol group represented by formula (1) above or the following formula (2), (3) or (4):

(2)

(3)

(4)

wherein said connecting group is a bivalent group having an ether group represented by formula (5), a bivalent group having an ester group represented by formula (6), a group represented by formula (8), or a group represented by formula (9):

(5)

wherein, $R^1$ is a straight- or branched-chain alkylene or alkenylene group having 1 to 22 carbons or an arylene group having 6 to 22 carbons, which may have one or more substituents; AO is an alkyleneoxy group having 1 to 4 carbons or an aryleneoxy group having 6 to 10 carbons; p is a number of 0 or 1; q is a number of 0 to 30; and q AO's may be the same or different from each other;

(6)

wherein, $R^2$ is a straight- or branched-chain alkylene or alkenylene group having 1 to 22 carbons or an arylene group having 6 to 22 carbons, which may have one or more substituents; r is a number of 0 to 30; AO is as defined above; and r AO's may be the same or different from each other;

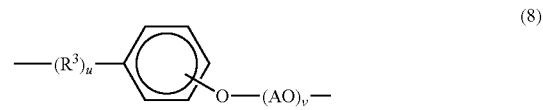
(8)

wherein, $R^3$ is a straight- or branched-chain alkylene or alkenylene group having 1 to 22 carbons which may have one or more substituents; u is a number of 0 or 1; v is a number of 0 to 30; AO is as defined above; and v AO's may be the same or different from each other; and

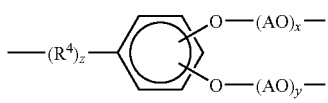

wherein, $R^4$ is a straight- or branched-chain alkylene or alkenylene group having 1 to 22 carbons which may have one or more substituents; z is a number of 0 or 1; x is a number of 0 to 30; y is a number of 0 to 30; AO is as defined above; and x and y AO's may be the same or different from each other.

2. The branched polyglycerol-modified silicone according to claim 1, wherein the average total number of the groups selected from the glycerol and glycidol groups represented by formulae (1), (2), (3) or (4) in the branched polyglycerol chain is from 3 to 201.

3. The branched polyglycerol-modified silicone according to claim 1, wherein said connecting group is a group represented by formula (7):

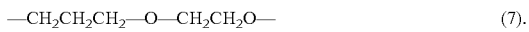

4. The branched polyglycerol-modified silicone according to claim 1, wherein said connecting group is a group represented by formula (10):

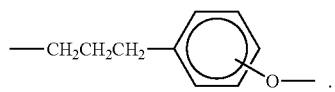

5. The branched polyglycerol-modified silicone according to claim 1, wherein said branched polyglycerol-modified silicone is a silicone represented by formula (11):

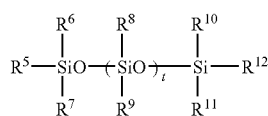

wherein, $R^5$, $R^6$, $R^7$, t $R^8$'s, t $R^9$'s, $R^{10}$, $R^{11}$, and $R^{12}$ each independently represent a connecting group to which a branched polyglycerol chain is connected, a straight- or branched-chain alkyl, alkenyl, or alkoxy group having 1 to 22 carbons which may have a substituent and may be substituted with fluorine atoms, or an aryl group having 6 to 22 carbons; at least one of $R^5$, $R^6$, $R^7$, t $R^8$'s, t $R^9$, $R^{10}$, $R^{11}$, $R^{12}$ is a connecting group to which a branched polyglycerol chain is bound; and t is a number of 0 to 10,000.

6. The branched polyglycerol-modified silicone according to claim 5, wherein one of $R^5$, $R^6$, and $R^7$ and one of $R^{10}$, $R^{11}$, and $R^{12}$ are connecting groups to which a branched polyglycerol chain is bound; and the other of $R^5$, $R^6$, $R^7$, $R^{10}$, $R^{12}$, t $R^8$'s, and t $R^9$'s each are a methyl group.

7. A method for producing the branched polyglycerol-modified silicone according to claim 1, comprising the step of adding 2,3-epoxy-1-propanol to a silicone having one or more functional groups selected from the group consisting of hydroxy, carboxy, amino, imino, mercapto and epoxy groups in the presence of an acid or base catalyst.

8. The method for producing a branched polyglycerol-modified silicone according to claim 7, wherein a metal hydroxide or metal alcolate is added to the silicone having at least one functional group selected from the group consisting of hydroxy, carboxy, amino, imino, mercapto and epoxy groups and after dehydration or dealcoholization 2,3-epoxy-1-propanol is added dropwise or intermittently to the resulting mixture.

9. A method for producing the branched polyglycerol-modified silicone according to claim 1, comprising the step of adding 2,3-epoxy-1-propanol to a silicone having a phenyl group substituted with at least one hydroxy group or with at least one polyoxyalkylene group having a hydroxy group at its end in the presence of an acid or base catalyst.

10. A method for producing a branched polyglycerol-modified silicone according to claim 9, comprising the step of adding a metal hydroxide or a metal alcolate to a silicone having a phenyl group substituted with at least one hydroxy group or with at least one polyoxyalkylene group having a hydroxy group at its end, conducting dehydration and dealcoholization and then adding 2,3-epoxy-1-propanol dropwise or intermittently to the resulting mixture.

11. A cosmetic comprising a branched polyglycerol-modified silicone according to claim 1.

12. The branched polyglycerol-modified silicone according to claim 5, wherein said connecting group is a group represented by formula (8) or (9).

13. The branched polyglycerol-modified silicone according to claim 12, wherein said connecting group is a group represented by formula (10):

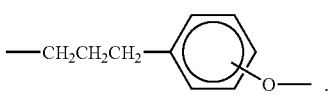

14. The branched polyglycerol-modified silicone according to claim 6, wherein said connecting group is a group represented by formula (8) or (9).

15. The branched polyglycerol-modified silicone according to claim 14, wherein said connecting group is a group represented by formula (10):

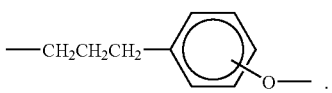

16. The branched polyglycerol-modified silicone according to claim 1, wherein 2 to 10 branched glycerol groups represented by formula (1) are connected via a connecting group to a silicon atom of said silicone.

17. The branched polyglycerol-modified silicone according to claim 1, wherein 2 to 5 branched glycerol groups represented by formula (1) are connected via a connecting group to a silicon atom of said silicone.

18. The branched polyglycerol-modified silicone according to claim 1, which comprises 2 to 101 groups of formula (4).

19. The branched polyglycerol-modified silicone according to claim 1, which comprises 3 to 101 groups of formula (4).

20. The branched polyglycerol-modified silicone according to claim 1, which comprises 3 to 51 groups of formula (4).

21. The branched polyglycerol-modified silicone according to claim 1, which comprises 3 to 26 groups of formula (4).

22. The branched polyglycerol-modified silicone according to claim 1, which comprises 3 to 11 groups of formula (4).

* * * * *

UNITED STATES PATENT AND TRADEMARK OFFICE
CERTIFICATE OF CORRECTION

PATENT NO. : 7,655,744 B2  Page 1 of 1
APPLICATION NO. : 10/949390
DATED : February 2, 2010
INVENTOR(S) : Seiichi Miyanaga It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1387 days.

Signed and Sealed this

Twenty-third Day of November, 2010

David J. Kappos
*Director of the United States Patent and Trademark Office*